(12) United States Patent
Johnson et al.

(10) Patent No.: US 11,839,527 B2
(45) Date of Patent: Dec. 12, 2023

(54) MANUALLY-OPERATED NEGATIVE PRESSURE WOUND THERAPY (NPWT) BANDAGE WITH IMPROVED PUMP EFFICIENCY, AUTOMATIC PRESSURE INDICATOR AND AUTOMATIC PRESSURE LIMITER

(71) Applicant: Cornell University, Ithaca, NY (US)

(72) Inventors: Timothy Johnson, Freeport, ME (US);
Charles Sears, Boxford, MA (US);
Sean Albert, Barrington, NH (US);
David Tortoriello, Topsfield, MA (US);
Orlando Soto, Amesbury, MA (US)

(73) Assignee: Cornell University, Ithaca, NY (US)

( * ) Notice: Subject to any disclaimer, the term of this patent is extended or adjusted under 35 U.S.C. 154(b) by 134 days.

(21) Appl. No.: 16/768,481

(22) PCT Filed: Dec. 6, 2018

(86) PCT No.: PCT/US2018/064178
§ 371 (c)(1),
(2) Date: May 29, 2020

(87) PCT Pub. No.: WO2019/113275
PCT Pub. Date: Jun. 13, 2019

(65) Prior Publication Data
US 2021/0169699 A1    Jun. 10, 2021

Related U.S. Application Data

(60) Provisional application No. 62/611,227, filed on Dec. 28, 2017, provisional application No. 62/595,398, filed on Dec. 6, 2017.

(51) Int. Cl.
*A61F 13/00*    (2006.01)
*A61M 1/00*    (2006.01)
(Continued)

(52) U.S. Cl.
CPC .... *A61F 13/00068* (2013.01); *A61F 13/0206* (2013.01); *A61M 1/915* (2021.05); *A61M 1/962* (2021.05); *A61M 39/24* (2013.01)

(58) Field of Classification Search
CPC .......... A61M 16/0057; A61M 16/0063; A61M 16/0075; A61M 16/0084; A61M 3/0262; A61M 1/682; A61M 2205/071; G01L 7/02

See application file for complete search history.

(56) References Cited

U.S. PATENT DOCUMENTS 3,486,504 A    12/1969    Austin, Jr.
3,874,387 A    4/1975    Barbieri
(Continued)

FOREIGN PATENT DOCUMENTS

CN    105457110    4/2016
WO    WO 02/087993    11/2002
(Continued)

OTHER PUBLICATIONS

Argenta et al., Vacuum-Assisted Closure: A New Method for Wound Control and Treatment: Clinical Experience, Annals of Plastic Surgery, Jun. 1997, vol. 38, No. 6, 563-577.
(Continued)

*Primary Examiner* — Erich G Herbermann
*Assistant Examiner* — Seth Han
(74) *Attorney, Agent, or Firm* — Pandiscio & Pandiscio

(57) ABSTRACT

A new and improved NPWT bandage which is simple, inexpensive, easy-to-use, small in size (including having a low profile), is atraumatic to the wound during use, has improved pump efficiency, incorporates an automatic pressure indicator for indicating the level of negative pressure created, and provides an automatic pressure limiter for limiting the level of negative pressure created.

53 Claims, 21 Drawing Sheets

PUMP ACTIVATED.
NEGATIVE PRESSURE CREATED INSIDE.

(51) Int. Cl.
   *A61F 13/02* (2006.01)
   *A61M 39/24* (2006.01)

(56) References Cited

U.S. PATENT DOCUMENTS

| | | | |
|---|---|---|---|
| 3,938,514 A * | 2/1976 | Boucher | A61M 3/0262 |
| | | | 222/206 |
| 4,073,294 A | 2/1978 | Stanley et al. | |
| 4,465,062 A | 8/1984 | Versaggi et al. | |
| 4,997,438 A | 3/1991 | Nipper | |
| 5,263,922 A | 11/1993 | Sova et al. | |
| 5,454,779 A | 10/1995 | Lurie et al. | |
| 5,478,333 A | 12/1995 | Asherman, Jr. | |
| 5,549,584 A | 8/1996 | Gross | |
| 5,562,107 A | 10/1996 | Lavender et al. | |
| 5,589,256 A | 12/1996 | Hansen et al. | |
| 5,636,643 A | 6/1997 | Argenta et al. | |
| 5,645,081 A | 7/1997 | Argenta et al. | |
| 5,788,463 A | 8/1998 | Chan | |
| 5,848,993 A * | 12/1998 | Tanhehco | A61M 1/682 |
| | | | D24/115 |
| 6,431,212 B1 | 8/2002 | Hayenga et al. | |
| 6,936,037 B2 | 8/2005 | Bubb et al. | |
| 6,951,553 B2 | 10/2005 | Bubb et al. | |
| 7,070,584 B2 | 7/2006 | Johnson et al. | |
| 7,290,660 B2 | 11/2007 | Tilman et al. | |
| 7,338,482 B2 | 3/2008 | Lockwood et al. | |
| 7,534,039 B2 | 5/2009 | Wu | |
| 7,569,742 B2 | 8/2009 | Haggstrom et al. | |
| 7,699,823 B2 | 4/2010 | Haggstrom et al. | |
| 7,763,769 B2 | 7/2010 | Johnson et al. | |
| 7,790,945 B1 | 9/2010 | Watson, Jr. | |
| 7,794,438 B2 | 9/2010 | Henley et al. | |
| 7,838,717 B2 | 11/2010 | Haggstrom et al. | |
| 7,874,731 B2 | 1/2011 | Turvey et al. | |
| 7,909,805 B2 | 3/2011 | Weston | |
| 7,942,866 B2 | 5/2011 | Radl et al. | |
| 7,951,100 B2 | 5/2011 | Hunt et al. | |
| 7,964,766 B2 | 6/2011 | Blott et al. | |
| 8,084,664 B2 | 12/2011 | Johnson et al. | |
| 8,187,210 B2 | 5/2012 | Hunt et al. | |
| 8,188,331 B2 | 5/2012 | Barta et al. | |
| 8,202,002 B2 | 6/2012 | McMahon et al. | |
| 8,207,392 B2 | 6/2012 | Haggstrom et al. | |
| 8,212,100 B2 | 7/2012 | Moore | |
| 8,257,326 B2 * | 9/2012 | Vitaris | A61F 13/025 |
| | | | 604/23 |
| 8,337,474 B2 | 12/2012 | Hu et al. | |
| 8,353,928 B2 | 1/2013 | Joshi | |
| 8,439,894 B1 | 5/2013 | Miller | |
| 8,460,255 B2 | 6/2013 | Joshi et al. | |
| 8,460,257 B2 | 6/2013 | Locke et al. | |
| 8,535,283 B2 | 9/2013 | Heaton et al. | |
| 8,545,466 B2 | 10/2013 | Andresen et al. | |
| 8,545,469 B2 | 10/2013 | Andresen et al. | |
| 8,569,566 B2 | 10/2013 | Blott et al. | |
| 8,604,265 B2 | 12/2013 | Locke et al. | |
| 8,632,523 B2 | 1/2014 | Eriksson et al. | |
| 8,679,079 B2 | 3/2014 | Heaton et al. | |
| 8,680,360 B2 | 3/2014 | Greener et al. | |
| 8,735,644 B2 | 5/2014 | Johnson et al. | |
| 8,764,732 B2 | 7/2014 | Hartwell | |
| 8,771,244 B2 | 7/2014 | Eckstein et al. | |
| 8,829,263 B2 | 9/2014 | Haggstrom et al. | |
| 8,961,481 B2 | 2/2015 | Hu et al. | |
| 9,033,942 B2 | 5/2015 | Vess | |
| 9,265,665 B2 | 2/2016 | Robinson et al. | |
| 9,302,033 B2 | 4/2016 | Riesinger | |
| 9,427,502 B2 | 8/2016 | Robinson et al. | |
| 9,427,505 B2 | 8/2016 | Askem et al. | |
| 9,545,465 B2 | 1/2017 | Allen et al. | |
| 9,561,312 B2 | 2/2017 | Heaton et al. | |
| 9,717,829 B2 | 8/2017 | Eriksson et al. | |
| 9,820,888 B2 | 11/2017 | Greener et al. | |
| 9,895,471 B2 | 2/2018 | Hu et al. | |
| 9,925,313 B2 | 3/2018 | Weston | |
| 9,968,488 B2 | 5/2018 | Zamierowski et al. | |
| 10,058,642 B2 | 8/2018 | Weston | |
| 10,064,984 B2 | 9/2018 | Locke et al. | |
| 10,123,909 B2 | 11/2018 | Hartwell | |
| 10,159,604 B2 | 12/2018 | Adie et al. | |
| 10,201,644 B2 | 2/2019 | Haggstrom et al. | |
| 10,426,875 B2 | 10/2019 | Blott et al. | |
| 10,485,907 B2 | 11/2019 | Huang | |
| 10,493,184 B2 | 12/2019 | Collinson et al. | |
| 10,548,776 B2 | 2/2020 | Greener et al. | |
| 10,610,414 B2 | 4/2020 | Hartwell et al. | |
| 10,653,823 B2 | 5/2020 | Bharti et al. | |
| 10,758,651 B2 | 9/2020 | Blott et al. | |
| 10,842,919 B2 | 11/2020 | Weston | |
| 11,071,653 B2 | 7/2021 | Hunt | |
| 11,110,010 B2 | 9/2021 | Hartwell | |
| 11,129,751 B2 | 9/2021 | Hartwell | |
| 11,179,276 B2 | 11/2021 | Hartwell | |
| 11,246,975 B2 | 2/2022 | Locke et al. | |
| 11,324,639 B2 | 5/2022 | Daich et al. | |
| 11,351,064 B2 | 6/2022 | Hartwell | |
| 11,433,176 B2 | 9/2022 | Hall et al. | |
| 2001/0029956 A1 | 10/2001 | Argenta et al. | |
| 2002/0111576 A1 | 8/2002 | Greene et al. | |
| 2003/0188754 A1 | 10/2003 | Heaton et al. | |
| 2004/0033750 A1 | 2/2004 | Everett et al. | |
| 2004/0054313 A1 | 3/2004 | Molan | |
| 2005/0070835 A1 | 3/2005 | Joshi | |
| 2005/0101940 A1 | 5/2005 | Radl et al. | |
| 2005/0143697 A1 | 6/2005 | Riesinger | |
| 2005/0175649 A1 | 8/2005 | Disalvo et al. | |
| 2005/0222528 A1 | 10/2005 | Weston | |
| 2005/0261642 A1 | 11/2005 | Weston | |
| 2006/0076069 A1 | 4/2006 | Haamer | |
| 2006/0079852 A1 | 4/2006 | Bubb et al. | |
| 2007/0055209 A1 | 3/2007 | Patel et al. | |
| 2008/0003274 A1 | 1/2008 | Kaiser | |
| 2008/0287892 A1 * | 11/2008 | Khan | A61M 1/985 |
| | | | 604/289 |
| 2008/0306456 A1 | 12/2008 | Riesinger | |
| 2009/0299256 A1 | 12/2009 | Barta et al. | |
| 2009/0326430 A1 * | 12/2009 | Frederiksen | A61F 13/0203 |
| | | | 156/289 |
| 2010/0063483 A1 | 3/2010 | Adahan | |
| 2010/0137775 A1 | 6/2010 | Hu et al. | |
| 2010/0160901 A1 | 6/2010 | Hu et al. | |
| 2010/0191197 A1 | 7/2010 | Braga et al. | |
| 2010/0286635 A1 | 11/2010 | Watson, Jr. | |
| 2010/0305490 A1 * | 12/2010 | Coulthard | A61M 1/962 |
| | | | 604/313 |
| 2010/0305524 A1 | 12/2010 | Vess et al. | |
| 2011/0087177 A2 | 4/2011 | Weston | |
| 2011/0106030 A1 | 5/2011 | Scholz | |
| 2011/0112492 A1 | 5/2011 | Bharti et al. | |
| 2011/0137270 A1 | 6/2011 | Hu et al. | |
| 2011/0196321 A1 | 8/2011 | Wudyka | |
| 2012/0035562 A1 | 2/2012 | Locke et al. | |
| 2012/0041401 A1 | 2/2012 | Chao et al. | |
| 2012/0109083 A1 | 5/2012 | Coulthard et al. | |
| 2012/0316538 A1 | 12/2012 | Heiser et al. | |
| 2013/0046223 A1 | 2/2013 | Schrammel | |
| 2013/0144231 A1 | 6/2013 | Hu et al. | |
| 2013/0209281 A1 | 8/2013 | Locke et al. | |
| 2013/0226115 A1 | 8/2013 | Robinson et al. | |
| 2013/0296816 A1 | 11/2013 | Greener | |
| 2013/0304007 A1 | 11/2013 | Toth | |
| 2013/0310809 A1 | 11/2013 | Armstrong et al. | |
| 2014/0088521 A1 | 3/2014 | Eriksson et al. | |
| 2014/0107597 A1 | 4/2014 | Hu et al. | |
| 2014/0171920 A1 | 6/2014 | Smith et al. | |
| 2014/0188061 A1 | 7/2014 | Locke et al. | |
| 2014/0221907 A1 | 8/2014 | Scholz et al. | |
| 2014/0241922 A1 | 8/2014 | Yang | |
| 2014/0243767 A1 | 8/2014 | Hu et al. | |
| 2014/0276498 A1 | 9/2014 | Connor et al. | |
| 2014/0343518 A1 | 11/2014 | Riesinger | |
| 2015/0005722 A1 | 1/2015 | Hu et al. | |
| 2015/0025486 A1 | 1/2015 | Hu et al. | |

(56) References Cited

U.S. PATENT DOCUMENTS

| | | |
|---|---|---|
| 2015/0057625 A1 | 2/2015 | Coulthard |
| 2015/0141941 A1 | 5/2015 | Allen et al. |
| 2015/0148761 A1 | 5/2015 | Hu et al. |
| 2015/0174304 A1 | 6/2015 | Askem et al. |
| 2015/0202354 A1* | 7/2015 | Wall ............... A61L 15/42 604/319 |
| 2015/0217032 A1 | 8/2015 | Allen et al. |
| 2015/0250931 A1 | 9/2015 | Bharti et al. |
| 2016/0045375 A1 | 2/2016 | Zurovcik |
| 2016/0184495 A1 | 6/2016 | Fouillet et al. |
| 2016/0199230 A1 | 7/2016 | Doshi et al. |
| 2016/0206792 A1* | 7/2016 | Worthley ............ A61F 13/0216 |
| 2016/0206793 A1 | 7/2016 | Robinson et al. |
| 2016/0287446 A1 | 10/2016 | Meixner et al. |
| 2016/0361205 A1 | 12/2016 | Mumby et al. |
| 2017/0080133 A1 | 3/2017 | Locke et al. |
| 2017/0112974 A1 | 4/2017 | Fujisaki |
| 2017/0128272 A1 | 5/2017 | Wu et al. |
| 2017/0143552 A1 | 5/2017 | Hartwell et al. |
| 2017/0172806 A1 | 6/2017 | Fung et al. |
| 2017/0181894 A1 | 6/2017 | Allen et al. |
| 2017/0181896 A1 | 6/2017 | Hartwell |
| 2017/0181897 A1 | 6/2017 | Hartwell |
| 2017/0209312 A1 | 7/2017 | Kanchagar et al. |
| 2017/0246113 A1 | 8/2017 | Blaskovich et al. |
| 2017/0266051 A1 | 9/2017 | Hartwell |
| 2017/0367895 A1 | 12/2017 | Holm et al. |
| 2017/0367896 A1 | 12/2017 | Holm et al. |
| 2018/0021178 A1 | 1/2018 | Locke et al. |
| 2018/0133065 A1 | 5/2018 | Hartwell |
| 2018/0140466 A1 | 5/2018 | Hunt |
| 2018/0140753 A1 | 5/2018 | Askem et al. |
| 2018/0168869 A1 | 6/2018 | Allen et al. |
| 2018/0185629 A1 | 7/2018 | Luckemeyer et al. |
| 2018/0221511 A1 | 8/2018 | Ohri et al. |
| 2018/0228482 A1 | 8/2018 | Madsen et al. |
| 2018/0243463 A1 | 8/2018 | Chatterjee et al. |
| 2018/0272052 A1 | 9/2018 | Locke et al. |
| 2018/0303676 A1 | 10/2018 | Bonn |
| 2018/0305468 A1 | 10/2018 | Tramontano et al. |
| 2018/0318477 A1 | 11/2018 | Eksteen |
| 2018/0369460 A1 | 12/2018 | Bonn |
| 2019/0099171 A1 | 4/2019 | Lichty, II et al. |
| 2019/0117575 A1 | 4/2019 | Blaskovich et al. |
| 2019/0183685 A1 | 6/2019 | McNulty et al. |
| 2019/0184076 A1 | 6/2019 | Gourlay |
| 2019/0269835 A1 | 9/2019 | Pinto et al. |
| 2019/0350965 A1 | 11/2019 | Ohri et al. |
| 2020/0000727 A1 | 1/2020 | Blaskovich et al. |
| 2020/0016081 A1 | 1/2020 | Ohri et al. |
| 2020/0069477 A1 | 3/2020 | Holm et al. |
| 2020/0078225 A1 | 3/2020 | Grillitsch et al. |
| 2020/0078499 A1 | 3/2020 | Gadde et al. |
| 2020/0085626 A1 | 3/2020 | Braga et al. |
| 2020/0086013 A1 | 3/2020 | Quintanar |
| 2020/0086016 A1 | 3/2020 | Bannister et al. |
| 2020/0093970 A1 | 3/2020 | Hunt et al. |
| 2020/0100945 A1 | 4/2020 | Albert et al. |
| 2020/0101207 A1 | 4/2020 | Weston et al. |
| 2020/0107964 A1 | 4/2020 | Locke et al. |
| 2020/0107967 A1 | 4/2020 | Holm et al. |
| 2020/0108235 A1 | 4/2020 | Locke et al. |
| 2020/0113741 A1 | 4/2020 | Rehbein et al. |
| 2020/0114050 A1 | 4/2020 | Collinson et al. |
| 2020/0114051 A1 | 4/2020 | Pratt et al. |
| 2020/0121509 A1 | 4/2020 | Locke et al. |
| 2020/0121510 A1 | 4/2020 | Hartwell et al. |
| 2020/0121511 A1 | 4/2020 | Locke et al. |
| 2020/0121512 A1 | 4/2020 | Locke et al. |
| 2020/0121833 A9 | 4/2020 | Askem et al. |
| 2020/0129341 A1 | 4/2020 | Coulthard et al. |
| 2020/0129674 A1 | 4/2020 | Moore et al. |
| 2020/0129675 A1 | 4/2020 | Robinson et al. |
| 2020/0155356 A1 | 5/2020 | Greener et al. |
| 2020/0268562 A1 | 8/2020 | Dunn |
| 2020/0282115 A1 | 9/2020 | Gardner et al. |
| 2021/0046224 A1 | 2/2021 | Blott et al. |
| 2021/0077669 A1 | 3/2021 | Weston |
| 2022/0000672 A1 | 1/2022 | Hunt |
| 2022/0000673 A1 | 1/2022 | Hartwell |
| 2022/0176032 A1 | 6/2022 | Randolph et al. |
| 2022/0226162 A1 | 7/2022 | Daich et al. |

FOREIGN PATENT DOCUMENTS

| | | |
|---|---|---|
| WO | WO 2005/051461 | 6/2005 |
| WO | WO 2007/068477 | 6/2007 |
| WO | WO 2008/048527 | 4/2008 |
| WO | WO 2009/124125 | 10/2009 |
| WO | WO 2009/124473 | 10/2009 |
| WO | WO 2010/068502 | 6/2010 |
| WO | WO 2010/121186 | 10/2010 |
| WO | WO 2011/049562 | 4/2011 |
| WO | WO 2011/162862 | 12/2011 |
| WO | WO 2012/021657 | 2/2012 |
| WO | WO 2012/038727 | 3/2012 |
| WO | WO 2012/151359 | 11/2012 |
| WO | WO 2013/039713 | 3/2013 |
| WO | WO 2014/039557 | 3/2014 |
| WO | WO 2014/140606 | 9/2014 |
| WO | WO 2014/145014 | 9/2014 |
| WO | WO 2015/052219 | 4/2015 |
| WO | WO 2016/094742 | 6/2016 |
| WO | WO 2016/182977 | 11/2016 |
| WO | WO-2016182977 A1 * 11/2016 ....... A61F 13/00068 |  |
| WO | WO 2017/053384 | 3/2017 |
| WO | WO 2019/113275 | 6/2019 |

OTHER PUBLICATIONS

Blackburn et al., Negative-Pressure Dressings as a Bolster for Skin Grafts, Annals of Plastic Surgery, May 1998, vol. 40, No. 5, 453-457.

Genecov et al., A Controlled Subatmospheric Pressure Dressing Increases the Rate of Skin Graft Donor Site Reepithelialization, Annals of Plastic Surgery, Mar. 1998, vol. 40, No. 3, 219-225.

Molnar et al., Single-Stage Approach to Skin Grafting the Exposed Skull, Jan. 5, 1999, vol. 105, No. 1, 174-177.

Morykwas et al., Vacuum-Assisted Closure: A New Method for Wound Control and Treatment: Animal Studies and Basic Foundation, Annals of Plastic Surgery, Jun. 1997, vol. 38, No. 6, 553-562.

Muensterer et al., A Simple Vacuum Dressing Reduces the Wound Infection Rate of Single-Incision Pediatric Endosurgical Appendectomy, JSLS (2011)15:147-150.

Seifarth et al., A Simple Postoperative Umbilical Negative-Pressure Dressing. Advances in Skin & Wound Care, vol. 26, No. 1 (2013), 26-29.

Sposato et al., Ambulant vacuum-assisted closure of skin-graft dressing in the lower limbs using a portable mini-VAC device. British Journal of Plastic Surgery, (2001), 54, 235-237.

* cited by examiner

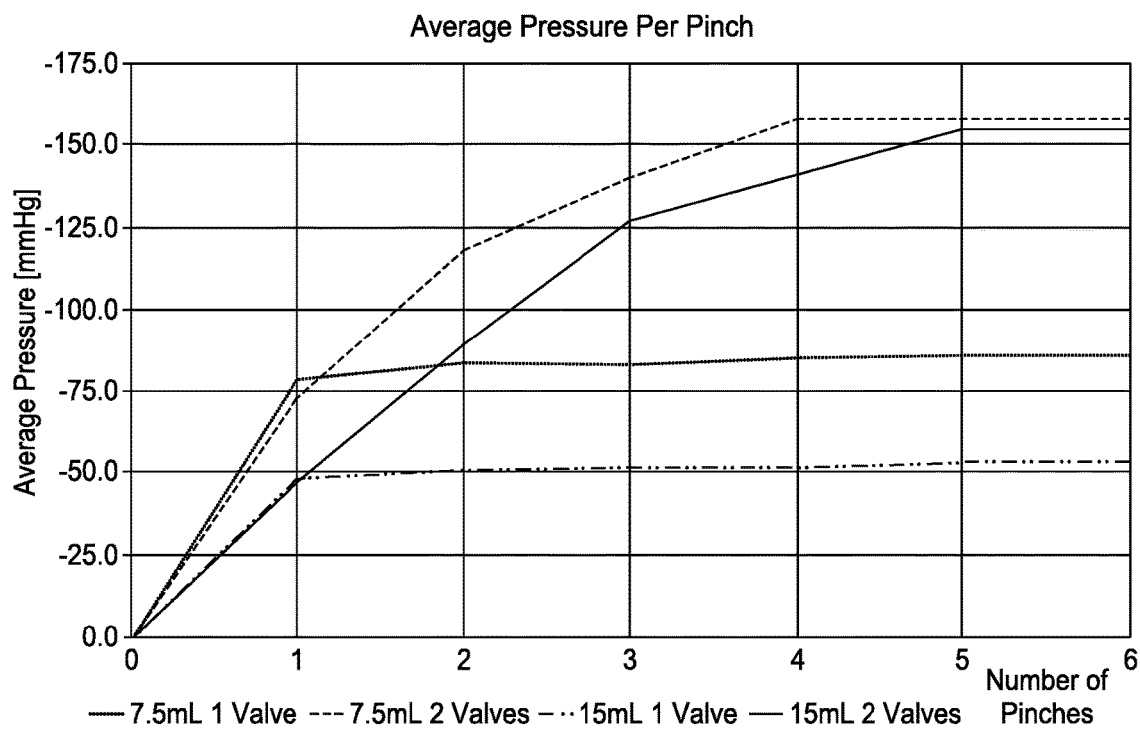

7.5 mL 1 Valve = 7.5 mL wound chamber, deformable body pump assembly with 1 one-way valve
7.5 mL 2 Valves = 7.5 mL wound chamber, deformable body pump assembly with 2 one-way valves
15 mL 1 Valve = 15 mL wound chamber, deformable body pump assembly with 1 one-way valve
15 mL 2 Valves = 15 mL wound chamber, deformable body pump assembly with 2 one-way valves Note: in the comparison shown in this figure, the volume of the pump chamber of the deformable pump body with 1 one-way valve is the same as the volume of the pump chamber of the deformable pump body with 2 one-way valves

FIG. 4A

UNBOX PRODUCT

UNWRAP PRODUCT FROM STERILE PACKAGING

PRODUCT UNPACKAGED AND READY FOR USE

REMOVE RELEASE LINER

APPLY PRODUCT TO WOUND SITE, AND REMOVE REMOVABLE STIFFENER

SQUEEZE SIDES OF PUMP TO EXPEL AIR FROM SEALED WOUND SITE

FULLY COLLAPSED PUMP BODY INDICATES NEGATIVE PRESSURE ACHIEVED

PATCH APPLIED.
AMBIENT PRESSURE INSIDE.

PUMP ACTIVATED.
NEGATIVE PRESSURE CREATED INSIDE.

PRESSURE INCREASES TOWARD AMBIENT.
PUMP EXPANDS TO RELAXED STATE.

SECTION 24 - 24

United States Patent US 11,839,527 B2

MANUALLY-OPERATED NEGATIVE PRESSURE WOUND THERAPY (NPWT) BANDAGE WITH IMPROVED PUMP EFFICIENCY, AUTOMATIC PRESSURE INDICATOR AND AUTOMATIC PRESSURE LIMITER

REFERENCE TO PENDING PRIOR PATENT APPLICATIONS

This patent application claims benefit of:
(1) prior U.S. Provisional Patent Application Ser. No. 62/595,398, filed Dec. 6, 2017 by Cornell University and Timothy Johnson et al. for MANUALLY-OPERATED NEGATIVE PRESSURE WOUND THERAPY (NPWT) BANDAGE WITH IMPROVED PUMP EFFICIENCY, AUTOMATIC PRESSURE INDICATOR AND AUTOMATIC PRESSURE LIMITER; and
(2) prior U.S. Provisional Patent Application Ser. No. 62/611,227, filed Dec. 28, 2017 by Cornell University and Timothy Johnson et al. for MANUALLY-OPERATED NEGATIVE PRESSURE WOUND THERAPY (NPWT) BANDAGE WITH IMPROVED PUMP EFFICIENCY, AUTOMATIC PRESSURE INDICATOR AND AUTOMATIC PRESSURE LIMITER.

The two (2) above-identified patent applications are hereby incorporated herein by reference.

FIELD OF THE INVENTION

This invention relates to bandages in general, and more particularly to negative pressure wound therapy (NPWT) bandages.

BACKGROUND OF THE INVENTION

Bandages are used to provide wound care during healing. More particularly, bandages generally provide a covering for a wound so as to shield the wound from contaminants and microbes during healing. Most bandages also provide a closure feature to help hold the edges of the wound in close apposition during healing. Bandages also frequently include gauze or the like to receive exudates emerging from the wound during healing.

Negative pressure wound therapy (NPWT) bandages apply a negative pressure to a wound during healing. This negative pressure helps reduce the likelihood of contaminants and microbes entering the wound during healing, helps draw exudates from the wound during healing, and can promote beneficial biological responses at the wound site. More particularly, NPWT bandages typically comprise (i) an absorbent dressing configured to make a fully-sealed chamber around the perimeter of a wound ("the wound chamber"), (ii) a source of negative pressure, and (iii) a conduit extending between the fully-sealed wound chamber and the source of negative pressure. As a result of this construction, the absorbent dressing can be applied to a wound so as to create a fully-sealed chamber around the perimeter of the wound, and the source of negative pressure can apply a negative pressure to the fully-sealed wound chamber, such that any contaminants and microbes present at the wound site are drawn away from the wound, exudates are drawn out of the wound, and beneficial biological responses are promoted at the wound site.

Most NPWT bandages are part of a large, complex NPWT system, in the sense that (i) the absorbent dressings are generally fairly large (e.g., they are sized to cover large open wounds), (ii) the sources of negative pressure are generally fairly large, and formed and located separate from the absorbent dressings (e.g., the sources of negative pressure typically comprise electrically-powered suction pumps or vacuum canisters), and (iii) the NPWT systems generally require substantial training to use. These NPWT systems also tend to be quite expensive.

Efforts have been made to provide a small, simplified and less expensive NPWT bandage where the source of negative pressure is integrated with the absorbent dressing. By way of example but not limitation, efforts have been made to provide an NPWT bandage where a manually-operated suction pump is integrated into the absorbent dressing. Unfortunately, current NPWT bandages integrating a suction pump with the absorbent dressing tend to suffer from a variety of deficiencies, e.g., they have a complex design, and/or are expensive, and/or are complicated to use, and/or are bulky (including having a high profile), and/or cause additional trauma to the wound during use, and/or have poor pump efficiency, and/or lack a way of indicating the level of negative pressure created, and/or lack a way of limiting the level of negative pressure created, etc. In this latter respect it should be appreciated that where too high a level of negative pressure is created, the NPWT bandage can cause trauma to the patient, e.g., blistering, capillary leakage, etc.

Thus there is a need for a new and improved NPWT bandage which is simple, inexpensive, easy-to-use, small in size (including having a low profile), is atraumatic to the wound during use, has improved pump efficiency, incorporates an automatic pressure indicator for indicating the level of negative pressure created, and provides an automatic pressure limiter for limiting the level of negative pressure created.

SUMMARY OF THE INVENTION

These and other objects of the invention are addressed by the provision and use of a new and improved NPWT bandage which is simple, inexpensive, easy-to-use, small in size (including having a low profile), is atraumatic to the wound during use, has improved pump efficiency, incorporates an automatic pressure indicator for indicating the level of negative pressure created, and provides an automatic pressure limiter for limiting the level of negative pressure created.

In one preferred form of the invention, there is provided a negative pressure wound therapy (NPWT) bandage for applying negative pressure to a wound, said NPWT bandage comprising:
a membrane configured for disposition over a wound so as to form a wound chamber between said membrane and the wound, said membrane comprising a wound-side surface, an atmosphere-side surface, and an opening extending through said membrane from said wound-side surface to said atmosphere-side surface; and
a pump assembly carried by said membrane, said pump assembly comprising:
a pump body comprising a wall structure disposed about a pump chamber, wherein at least a portion of said wall structure is resilient;
a wound-side passageway extending through said wall structure and communicating with the wound chamber through said opening formed in said membrane;
a wound-side one-way valve disposed in said wound-side passageway, said wound-side one-way valve being configured to allow fluid to flow through said wound-side passageway from the wound chamber to said pump chamber but to prevent fluid from flowing through said wound-side passageway from said pump chamber to the wound chamber;

an atmosphere-side passageway extending through said wall structure and connecting said pump chamber and the atmosphere; and an atmosphere-side one-way valve disposed in said atmosphere-side passageway, said atmosphere-side one-way valve being configured to allow fluid to flow through said atmosphere-side passageway from said pump chamber to the atmosphere but to prevent fluid from flowing through said atmosphere-side passageway from the atmosphere to said pump chamber;

such that when a compressive force is applied to said wall structure of said pump body, fluid within said pump chamber will be forced out of said pump chamber via said atmosphere-side passageway, and when the compressive force applied to said wall structure of said pump body is thereafter reduced, fluid within the wound chamber will be drawn into said pump chamber through said wound-side passageway.

Preferably, the NPWT bandage is configured so that when the pressure differential between the pressure of the fluid within said pump chamber and atmospheric pressure is below a predetermined threshold, said pump body of said pump assembly will assume a substantially fully expanded configuration, and when said pressure differential between the pressure of the fluid within said pump chamber and atmospheric pressure is above said predetermined threshold, said pump body of said pump assembly will assume a substantially fully collapsed configuration.

Even more preferably, the NPWT bandage is configured so that said pump body abruptly changes state between said substantially fully expanded configuration and said substantially fully collapsed configuration, and between said substantially fully collapsed configuration and said substantially fully expanded configuration, as said pressure differential crosses said predetermined threshold so as to effectively constitute a substantially "binary state" device.

In another preferred form of the invention, there is provided a method for applying negative pressure to a wound, the method comprising:

providing a negative pressure wound therapy (NPWT) bandage comprising:
  a membrane configured for disposition over a wound so as to form a wound chamber between said membrane and the wound, said membrane comprising a wound-side surface, an atmosphere-side surface, and an opening extending through said membrane from said wound-side surface to said atmosphere-side surface; and
  a pump assembly carried by said membrane, said pump assembly comprising:
    a pump body comprising a wall structure disposed about a pump chamber, wherein at least a portion of said wall structure is resilient;
    a wound-side passageway extending through said wall structure and communicating with the wound chamber through said opening formed in said membrane;
    a wound-side one-way valve disposed in said wound-side passageway, said wound-side one-way valve being configured to allow fluid to flow through said wound-side passageway from the wound chamber to said pump chamber but to prevent fluid from flowing through said wound-side passageway from said pump chamber to the wound chamber;
    an atmosphere-side passageway extending through said wall structure and connecting said pump chamber and the atmosphere; and
    an atmosphere-side one-way valve disposed in said atmosphere-side passageway, said atmosphere-side one-way valve being configured to allow fluid to flow through said atmosphere-side passageway from said pump chamber to the atmosphere but to prevent fluid from flowing through said atmosphere-side passageway from the atmosphere to said pump chamber;
  such that when a compressive force is applied to said wall structure of said pump body, fluid within said pump chamber will be forced out of said pump chamber via said atmosphere-side passageway, and when the compressive force applied to said wall structure of said pump body is thereafter reduced, fluid within the wound chamber will be drawn into said pump chamber through said wound-side passageway;

positioning said negative pressure wound therapy (NPWT) bandage over the wound so as to form a wound chamber between said membrane and the wound; and applying a compressive force to said wall structure of said pump body, and thereafter reducing the compressive force applied to said wall structure of said pump body, so as to apply negative pressure to the wound.

In another preferred form of the invention, there is provided a negative pressure wound therapy (NPWT) bandage for applying negative pressure to a wound, said NPWT bandage comprising:

a membrane configured for disposition over a wound so as to form a wound chamber between said membrane and the wound, said membrane comprising a wound-side surface, an atmosphere-side surface, and an opening extending through said membrane from said wound-side surface to said atmosphere-side surface; and a pump carried by said membrane and comprising a wall chamber disposed about a pump chamber, wherein at least a portion of said wall chamber is resilient, and further wherein said pump chamber communicates with the wound chamber through said opening formed in said membrane;

wherein no part of said pump chamber is defined by the wound.

In another preferred form of the invention, there is provided a negative pressure wound therapy (NPWT) bandage for applying negative pressure to a wound, said NPWT bandage comprising:

a membrane configured for disposition over a wound so as to form a wound chamber between said membrane and the wound, said membrane comprising a wound-side surface, an atmosphere-side surface, and an opening extending through said membrane from said wound-side surface to said atmosphere-side surface; and a pump carried by said membrane and comprising a wall chamber disposed about a pump chamber, wherein at least a portion of said wall chamber is resilient, and further wherein said pump chamber communicates with the wound chamber through said opening formed in said membrane;

wherein said pump does not apply positive pressure to the wound.

In another preferred form of the invention, there is provided a negative pressure wound therapy (NPWT) bandage for applying negative pressure to a wound, said NPWT bandage comprising:

a membrane configured for disposition over a wound so as to form a wound chamber between said membrane and the wound, said membrane comprising a wound-side surface, an atmosphere-side surface, and an opening extending through said membrane from said wound-side surface to said atmosphere-side surface; and a pump carried by said membrane and comprising a wall chamber disposed about a pump chamber, wherein at least a portion of said wall chamber is resilient, and further wherein said pump chamber communicates with the wound chamber through said opening formed in said membrane;

wherein said pump is connected to the wound chamber such that a reduction in the volume of the pump chamber does not cause a change in pressure in the wound chamber.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 4A is a schematic view showing, for two different size wound chambers (i.e., a 7.5 mL wound chamber and a 15 mL wound chamber), a maximum negative pressure that may be established with (i) a deformable pump body having two one-way valves (with one one-way valve being disposed on either side of the deformable pump body), and (ii) a deformable pump body having a single one-way valve (note: in the comparison shown in FIG. 4A, the volume of the pump chamber of the deformable pump body with 1 one-way valve is the same as the volume of the pump chamber of the deformable pump body with 2 one-way valves);

DETAILED DESCRIPTION OF THE PREFERRED EMBODIMENTS

Figure 1:
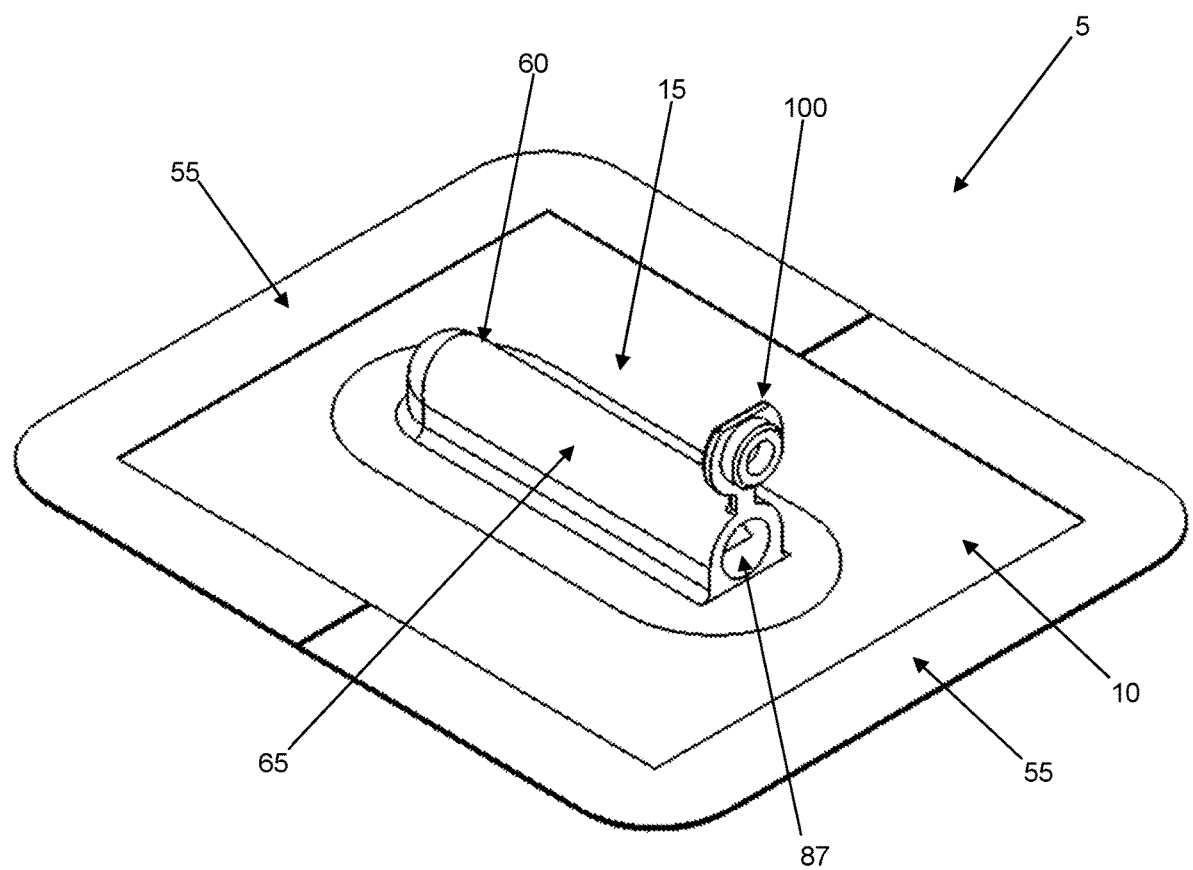
FIGS. 1-4 are schematic views showing a new and improved NPWT bandage formed in accordance with the present invention, with FIGS. 2 and 3 being exploded views.
Figure 2:
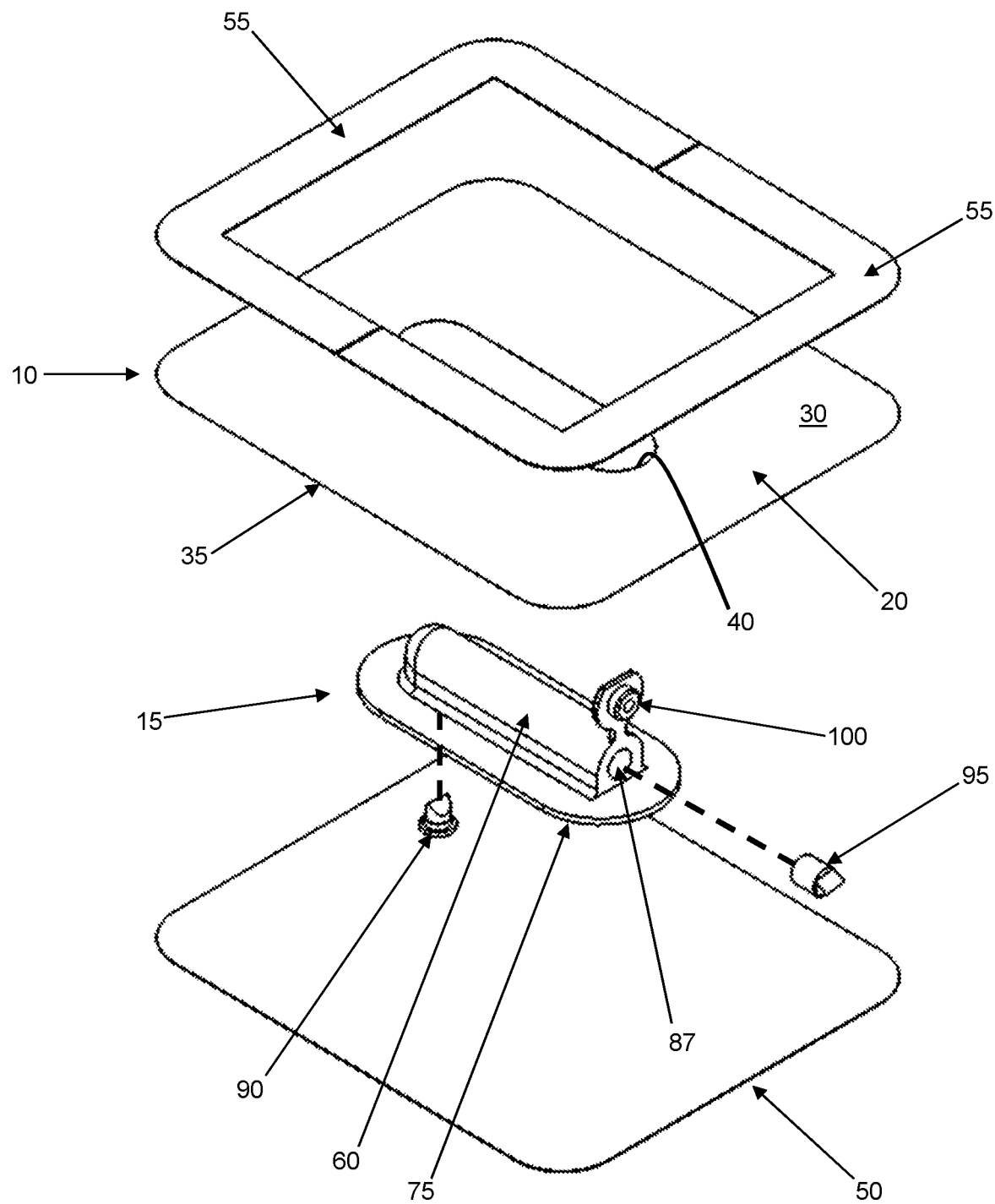
Figure 3:
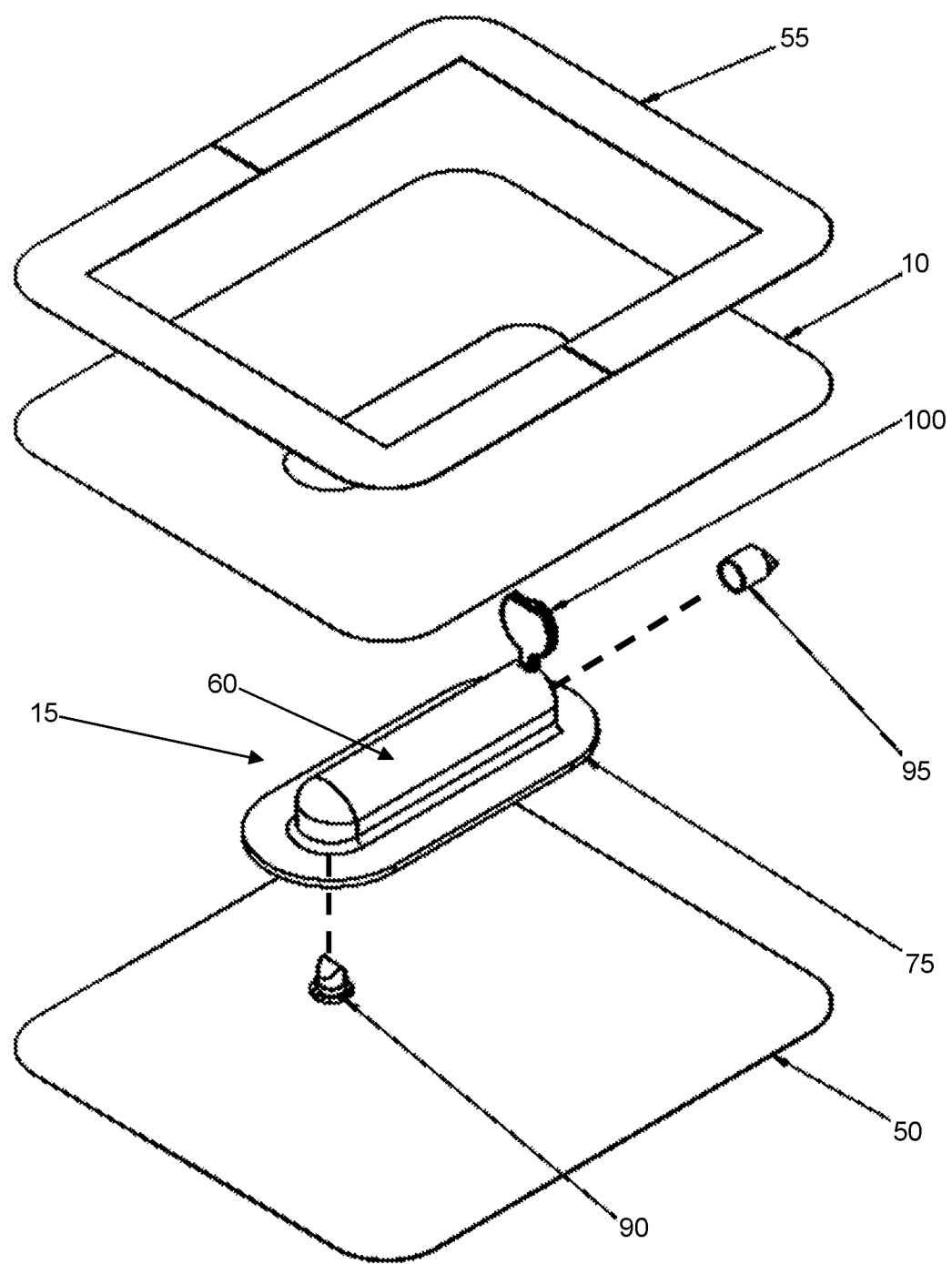
Figure 4:
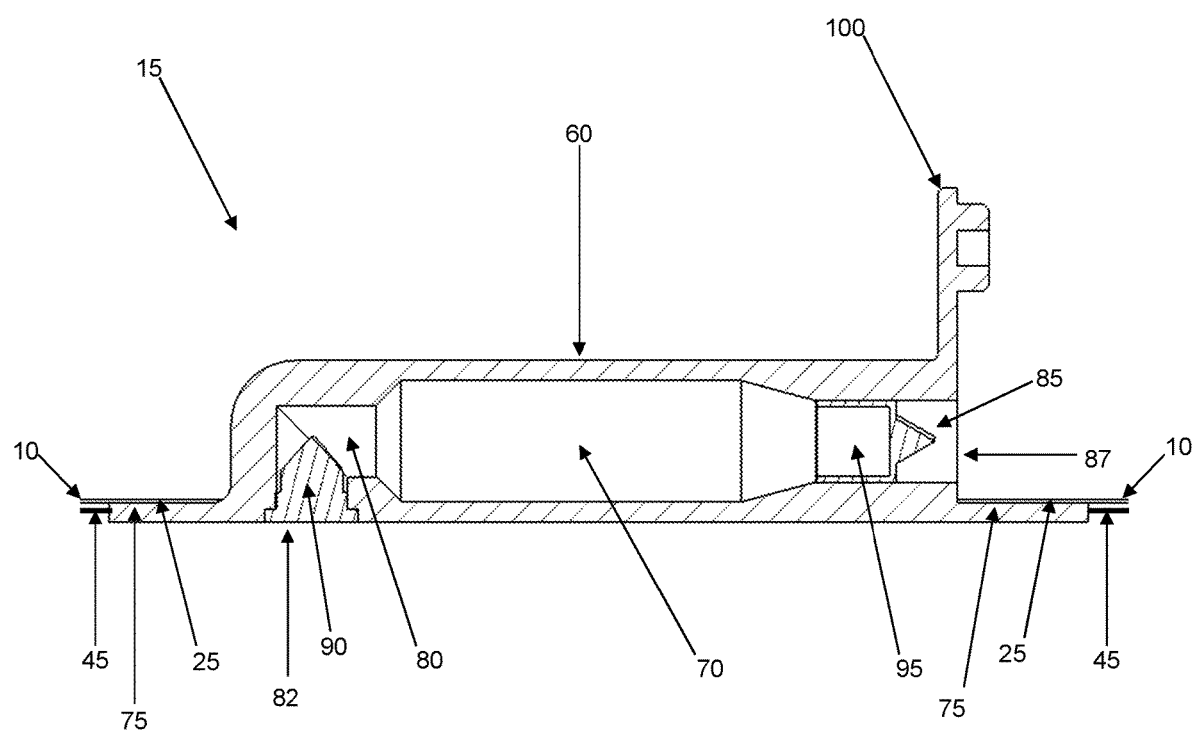

The present invention comprises the provision and use of a new and improved NPWT bandage which is simple, inexpensive, easy-to-use, small in size (including having a low profile), is atraumatic to the wound during use, has improved pump efficiency, incorporates an automatic pressure indicator for indicating the level of negative pressure created, and provides an automatic pressure limiter for limiting the level of negative pressure created.

The Manually-Operated Negative Pressure Wound Therapy (NPWT) Bandage in General More particularly, and looking first at FIGS. 1-4, there is shown a manually-operated negative pressure wound therapy (NPWT) bandage 5 having improved pump efficiency, an automatic pressure indicator for indicating the level of negative pressure created, and an automatic pressure limiter for limiting the level of negative pressure created.

NPWT bandage 5 generally comprises a membrane (or sheet) 10 and a pump assembly 15.

As will hereinafter be discussed, membrane 10 is configured to make a fully-sealed chamber around the perimeter of a wound, whereby to define a wound chamber.

And as will hereinafter be discussed, pump assembly 15 is configured to apply a negative pressure to the fully-sealed wound chamber, such that any contaminants and microbes present at the wound site are drawn away from the wound, exudates are drawn out of the wound, and beneficial biological responses are promoted at the wound site. Significantly, pump assembly 15 is designed to provide improved pump efficiency, an automatic pressure indicator for indicating the level of negative pressure created, and an automatic pressure limiter for limiting the level of negative pressure created, as will hereinafter be discussed.

The Membrane

More particularly, membrane 10 comprises a flat planar sheet 20 formed out of a flexible, substantially air-impermeable material, e.g., Tegaderm from 3M Company (which has also been known as the Minnesota Mining and Manufacturing Company), so that it can conform to body contours and form a substantially air-tight chamber around the perimeter of a wound (i.e., the wound chamber). Membrane 10 is characterized by a wound-side surface 25 and an atmosphere-side surface 30. Membrane 10 is also characterized by an outer perimeter 35 and an inner opening 40.

An adhesive 45 is preferably disposed on wound-side surface 25 of membrane 10. A release liner 50 is preferably disposed on wound-side surface 25 atop adhesive 45 so as to keep adhesive 45 covered until use.

A removable stiffener 55 is preferably disposed on atmosphere-side surface 30 of membrane 10. Removable stiffener 55 serves to facilitate manipulation of NPWT bandage 5 (and particularly membrane 10) during removal of the NPWT bandage from its sterile packaging and during positioning of the NPWT bandage about a wound. Removable stiffener 55 is intended to be removed from membrane 10 once NPWT bandage 5 has been secured about the wound site. Removable stiffener 55 may be provided as a single element or, more preferably, removable stiffener 55 is provided as a pair of elements so as to facilitate removal from membrane 10 after NPWT bandage 5 has been secured about the wound site.

The Pump Assembly

Figure 5:
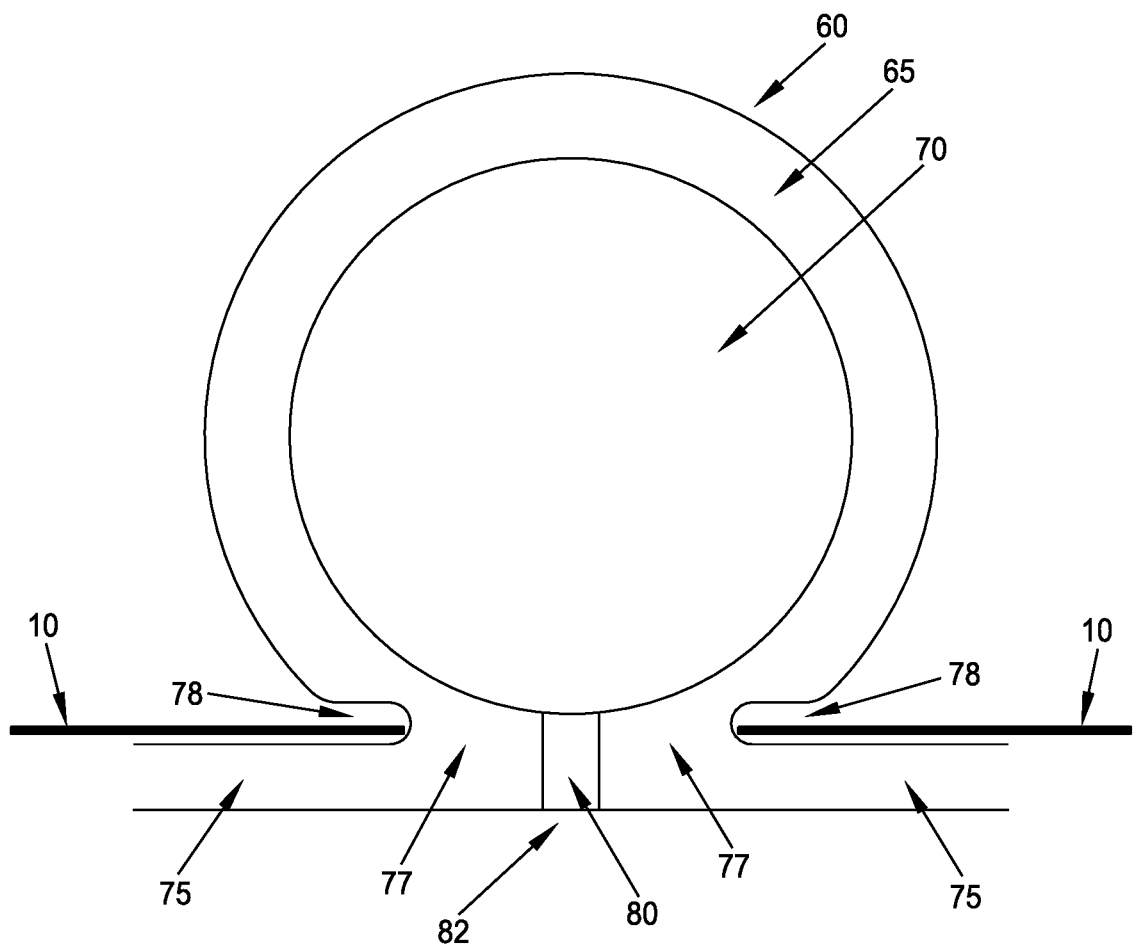
FIGS. 5 and 6 are schematic views showing the pump body of the pump assembly of the NPWT bandage shown in FIGS. 1-4 in its substantially fully expanded configuration (FIG. 5) and in its substantially fully collapsed configuration (FIG. 6)

Pump assembly 15 comprises a pump body 60 having a generally cylindrical shape and comprising a side wall 65 and an inner chamber 70. Pump body 60 is formed out of a resilient material, e.g., silicone, such that side wall 65 may be compressed inwardly by the application of an external force (e.g., squeezing by the thumb and forefinger of a user) and will then attempt to return to its original uncompressed state when the external force is removed. A pump flange 75 is preferably formed on one side of pump body 60. As will hereinafter be discussed in further detail, pump body 60 extends through inner opening 40 of membrane 10, and the upper surface of pump flange 75 is secured to the wound-side surface 25 of membrane 10 so that pump assembly 15 is secured to, and carried by, membrane 10. Pump flange 75 is preferably formed out of a flexible material so that it can conform (to at least a limited extent) to body contours. In one form of the invention, pump body 60 and pump flange 75 are formed integral with one another out of the same material, e.g., silicone. In one preferred form of the invention, side wall 65 of pump body 60 and pump flange 75 merge at a neck 77 (FIG. 5). And in one preferred form of the invention, neck 77 has a relatively small width relative to the full diameter of pump body 60, with recesses 78 extending inwardly between membrane 10 and pump body 60, such that pump body 60 is mounted to pump flange 75 but is still free to radially compress/radially expand with minimal interference from pump flange 75. A wound-side passageway 80 is formed in pump body 60 and communicates with inner chamber 70. Wound-side passageway 80 opens on the exterior of pump body 60 at a wound-side port 82. An atmosphere-side passageway 85 is formed in pump body 60 and also communicates with inner chamber 70. Atmosphere-side passageway 85 opens on the exterior of pump body 60 at an atmosphere-side port 87.

A wound-side one-way valve 90 is disposed in wound-side passageway 80 and is configured to permit fluid to enter inner chamber 70 through wound-side passageway 80 but to prevent fluid from exiting inner chamber 70 through wound-side passageway 80.

An atmosphere-side one-way valve 95 is disposed in atmosphere-side passageway 85 and is configured to permit fluid to exit inner chamber 70 through atmosphere-side passageway 85 but to prevent fluid from entering inner chamber 70 through atmosphere-side passageway 85.

As a result of this construction, when pump body 60 of pump assembly 15 is manually squeezed (e.g., by applying a compressive force to side wall 65 of pump body 60 with the thumb and forefinger of a user), fluid (e.g., air, liquid, etc.) within inner chamber 70 will be forced out of inner chamber 70 via atmosphere-side passageway 85, and when pump body 60 of pump assembly 15 is thereafter released (e.g., by relaxing the compressive force applied to side wall 65 of pump body 60 by the thumb and forefinger of a user), fluid (e.g., air, liquid, etc.) below wound-side surface 25 of membrane 10 (e.g., air, liquid, etc. within the wound chamber) will be drawn into inner chamber 70 through wound-side passageway 85 as the resilient side wall of the pump body returns to its uncompressed state.

Note that when pump body 60 of pump assembly 15 is manually squeezed, fluid (e.g., air, liquid, etc.) within inner chamber 70 is prevented from exiting inner chamber 70 through wound-side passageway 80 due to the one-way operation of wound-side one-way valve 90, and when pump body 60 of pump assembly 15 is thereafter released, air from the atmosphere is prevented from being drawn into inner chamber 70 through atmosphere-side passageway 85 due to the one-way operation of atmosphere-side one-way valve 95.

Thus it will be appreciated that repeatedly manually squeezing and releasing pump body 60 of pump assembly 15 will apply suction to the wound chamber disposed below wound-side surface 25 of membrane 10, whereby to create negative pressure at the wound site.

It should be appreciated that the present invention's approach of providing a pump assembly utilizing two one-way valves disposed on either side of a deformable pump body with an in-line configuration (i.e., wound-side one-way valve 90 and atmosphere-side one-way valve 95 disposed on either side of deformable pump body 60) provides a number of significant advantages which are not achievable with the prior art's approach of providing a deformable pump body utilizing a single one-way valve.

More particularly, and as will hereinafter be discussed, the present invention's approach of providing a pump assembly utilizing two one-way valves disposed on either side of a deformable pump body with an in-line configuration (i.e., wound-side one-way valve 90 and atmosphere-side one-way valve 95 disposed on either side of deformable pump body 60) allows substantially the same maximum negative pressure to be established at the wound site regardless of the size of the wound chamber. This is not achievable with the prior art's approach of providing a deformable pump body utilizing a single one-way valve.

In addition, the present invention's approach of providing a pump assembly utilizing two one-way valves disposed on either side of a deformable pump body with an in-line configuration (i.e., wound-side one-way valve 90 and atmosphere-side one-way valve 95 disposed on either side of deformable pump body 60) allows a greater constant selected maximum negative pressure to be achieved at the wound site than can be achieved at the wound site using a deformable pump body with a single one-way valve (which is reflective of the prior art's approach).

More particularly, FIG. 4A shows, for two different size wound chambers (i.e., a 7.5 mL wound chamber and a 15 mL wound chamber), a maximum negative pressure that may be established with (i) a deformable pump body having two one-way valves (with one one-way valve being disposed on either side of the deformable pump body), and (ii) a deformable pump body having a single one-way valve (note: in the comparison shown in FIG. 4A, the volume of the pump chamber of the deformable pump body with 1 one-way valve is the same as the volume of the pump chamber of the deformable pump body with 2 one-way valves).

Inherent in FIG. 4A are a number of significant aspects of the present invention.

First, FIG. 4A shows that using a deformable pump body having two one-way valves (with one one-way valve being disposed on either side of the deformable pump body) to evacuate the wound chamber lets you establish substantially the same maximum negative pressure in the wound chamber regardless of the size of the wound chamber (i.e., it yields approximately −150.0 mm Hg for a 7.5 mL wound chamber and approximately −150.0 mm Hg for a 15 mL wound chamber), whereas using a deformable pump body having a single one-way valve does not (i.e., it yields approximately −80.0 mm Hg for a 7.5 mL wound chamber and approximately −50.0 mm Hg for a 15 mL wound chamber). Thus, the NPWT bandage of the present invention allows substantially the same maximum negative pressure to be established at the wound site regardless of the size of the wound chamber, whereas prior art NPWT bandages do not.

This unique feature of the present invention is clinically significant, inasmuch as (i) it is generally desirable to establish a selected maximum negative pressure at the wound site (e.g., between about 60 mm Hg and about 180 mm Hg), and (ii) it is generally difficult to know in advance the volume of the wound chamber (e.g., due to variations in medical applications, variations in patient anatomy, etc.). Thus, inasmuch as the NPWT bandage of the present invention allows substantially the same maximum negative pressure to be established at the wound site regardless of the size of the wound chamber, the present invention allows the NPWT bandage to be engineered in advance (e.g., at the time of manufacture) to establish a selected maximum negative pressure at the wound site, whereas prior art NPWT bandages do not.

Second, FIG. 4A shows that using a deformable pump body having two one-way valves (with one one-way valve being disposed on either side of the deformable pump body) to evacuate the wound chamber lets you establish a substantially higher maximum negative pressure in the wound chamber (i.e., it yields approximately −150.0 mm Hg for a 7.5 mL wound chamber and approximately −150.0 mm Hg for a 15 mL wound chamber) than can be established using a deformable pump body having a single one-way valve (i.e., it yields approximately −80.0 mm Hg for a 7.5 mL wound chamber and approximately −50.0 mm Hg for a 15 mL wound chamber). Thus, the NPWT bandage of the present invention allows a substantially higher maximum negative pressure to be established at the wound site.

Note also that the pressure within inner chamber 70 of pump body 60 is generally equal to the pressure below wound-side surface 25 of membrane 10 (i.e., the pressure within inner chamber 70 of pump body 60 is generally equal to the pressure within the wound chamber).

In one preferred form of the invention, pump assembly 15 also comprises a removable cap 100. Removable cap 100 is configured to selectively close off atmosphere-side passageway 85 to fluid flow when removable cap 100 is inserted into atmosphere-side passageway 85 so as to close off atmosphere-side port 87.

Pump assembly 15 is mounted to membrane 10 such that pump assembly 15 is carried by membrane 10. More particularly, pump assembly 15 is mounted to membrane 10 by (i) passing pump body 60 of pump assembly 15 through inner opening 40 of membrane 10, (ii) bringing pump flange 75 up against wound-side surface 25 of membrane 10, and then (iii) adhering pump flange 75 to wound-side surface 25 of membrane 10 (e.g., by bonding, gluing, etc.). Note that pump assembly 15 and membrane 10 make a substantially air-tight connection.

Significantly, pump body 60 of pump assembly 15 is carefully configured to provide (i) improved pump efficiency, (ii) an automatic pressure indicator for indicating the level of negative pressure created, and (iii) an automatic pressure limiter for limiting the level of negative pressure created, as will hereinafter be discussed.

More particularly, pump body 60 of pump assembly 15 is specifically configured so that the pump body will abruptly change state between (i) a substantially fully expanded configuration where side wall 65 of pump body 60 and inner chamber 70 of pump body 60 have a substantially circular cross-section (see FIG. 5) when the pressure differential between the pressure of the fluid within inner chamber 70 and atmospheric pressure is below a given threshold, and (ii) a substantially fully collapsed configuration where side wall 65 of pump body 60 bows inwardly (see FIG. 6) when the pressure differential between the pressure of the fluid within inner chamber 70 and atmospheric pressure exceeds a given threshold.

Figure 6:
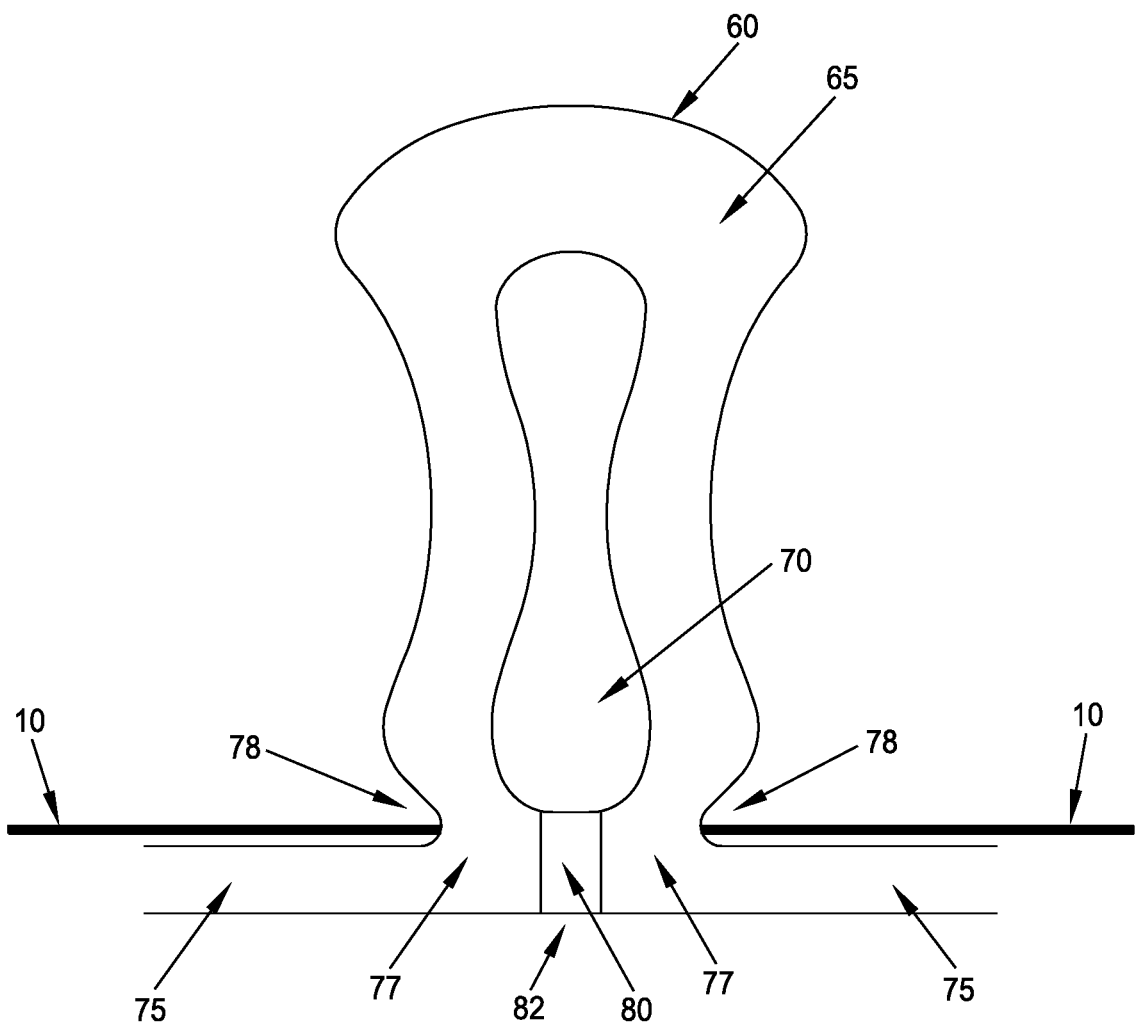

Specifically, when the pressure differential between the pressure of the fluid within inner chamber 70 and atmospheric pressure is below a given threshold, pump body 60 of pump assembly 15 will assume its substantially fully expanded configuration (FIG. 5), and when the pressure differential between the pressure of the fluid within inner chamber 70 and atmospheric pressure is above a given threshold, pump body 60 of pump assembly 15 will assume its substantially fully collapsed configuration (FIG. 6).

Figure 7:
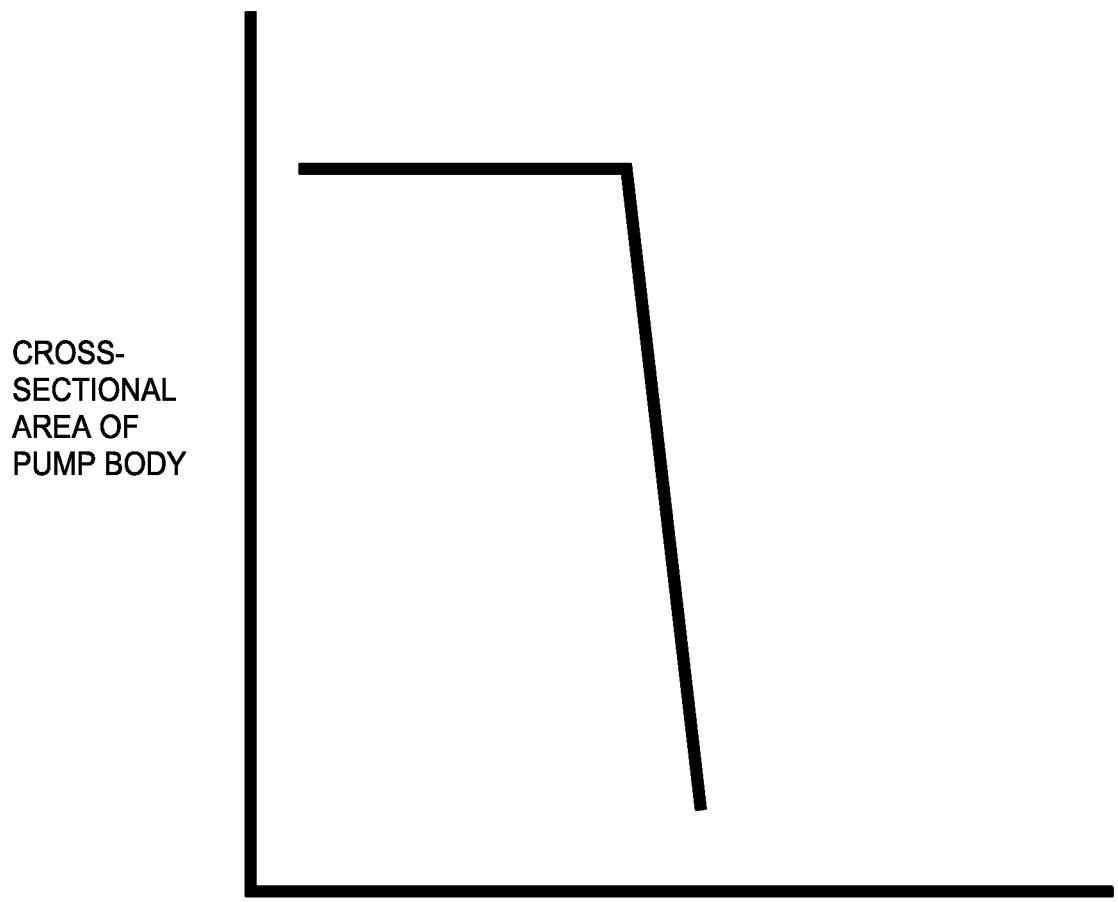
FIG. 7 is a schematic view showing how the pump body of the pump assembly of the NPWT bandage shown in FIGS. 1-4 abruptly changes state between its substantially fully expanded configuration and its substantially fully collapsed configuration.

Significantly, pump body 60 of pump assembly 15 is configured so that it will abruptly change state between its substantially fully expanded configuration (FIG. 5) and its substantially fully collapsed configuration (FIG. 6) when the pressure differential between the pressure of the fluid within inner chamber 70 and atmospheric pressure crosses the aforementioned given threshold. See FIG. 7, which is a graph showing the relationship between the diameter of side wall 65 of pump body 60 and the pressure differential between the pressure of a fluid within inner chamber 70 and atmospheric pressure. Thus, pump assembly 15 is specifically configured to essentially behave as a substantially "binary state" device—it is either substantially fully expanded (FIG. 5) or substantially fully collapsed (FIG. 6). In this respect it should be appreciated that, as used herein, the term "substantially "binary state" device" is intended to refer to a device which is inclined to assume either a substantially fully expanded condition or a substantially fully collapsed condition and, as used herein, the term "substantially "binary state" behavior" is intended to refer to the inclination of a device to assume either a substantially fully expanded condition or a substantially fully collapsed condition.

Note that the substantially "binary state" behavior of pump body 60 is a consequence of forming the pump body with a side wall 65 having a substantially circular cross-section, which gives the pump body an "over-the-center" deformation characteristic, i.e., the side wall of pump body 60 has a "failure" mode where it abruptly transitions from its substantially fully expanded configuration to its substantially fully collapsed configuration, and has a "restoration" mode where it abruptly transitions from its substantially fully collapsed configuration to its substantially fully expanded configuration. See FIG. 7. Note that by forming pump assembly 15 so that side wall 65 of pump body 60 and pump flange 75 merge at a neck 77 (FIG. 5), with neck 77 having a relatively small width relative to the full diameter of pump body 60, and with recesses 78 extending inwardly between membrane 10 and pump body 60, pump body 60 has a substantially circular cross-section over substantially its entire circumference, with pump body 60 free to radially compress/radially expand with minimal interference from pump flange 75, so that pump body 60 can exhibit substantially "binary state" behavior.

Figure 8:
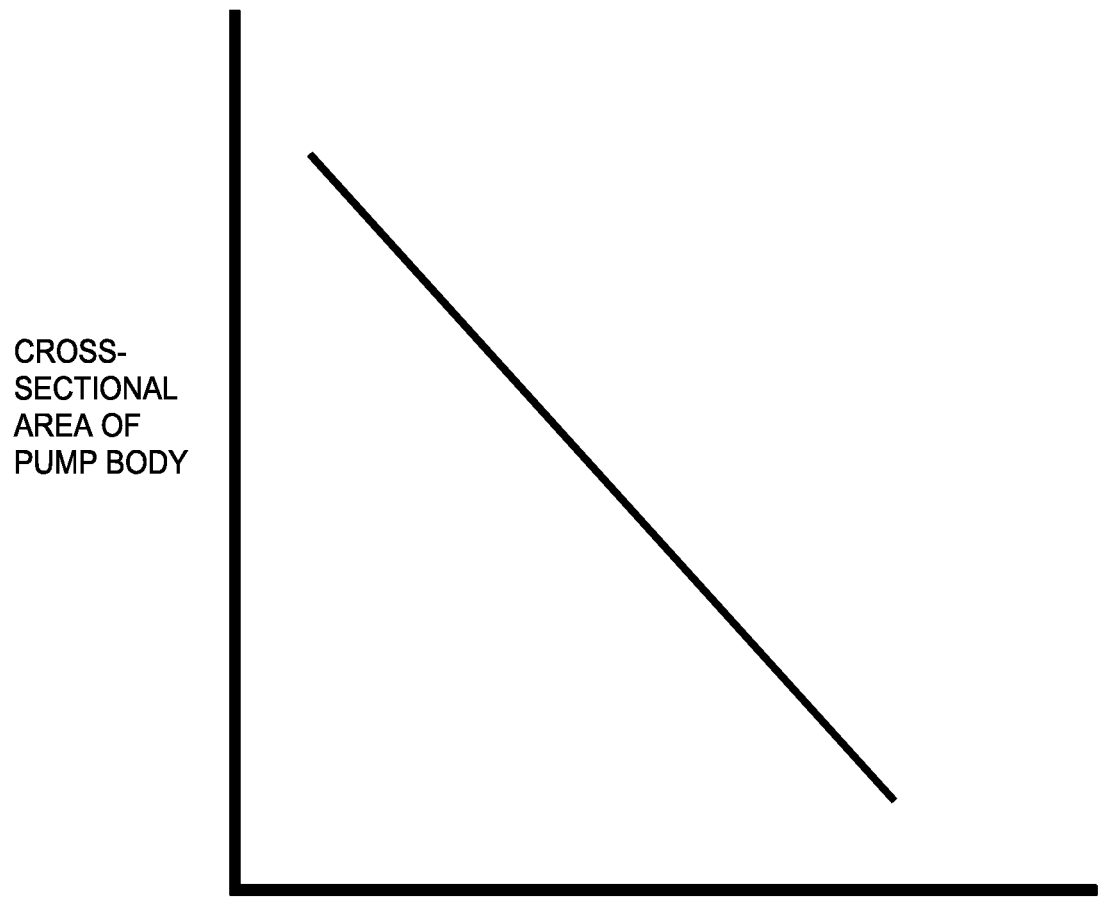
FIG. 8 is a schematic view showing how the pump bodies of the pump assemblies of prior art NPWT bandages gradually change state between their substantially fully expanded configuration and their substantially fully collapsed configuration.
Figure 9:
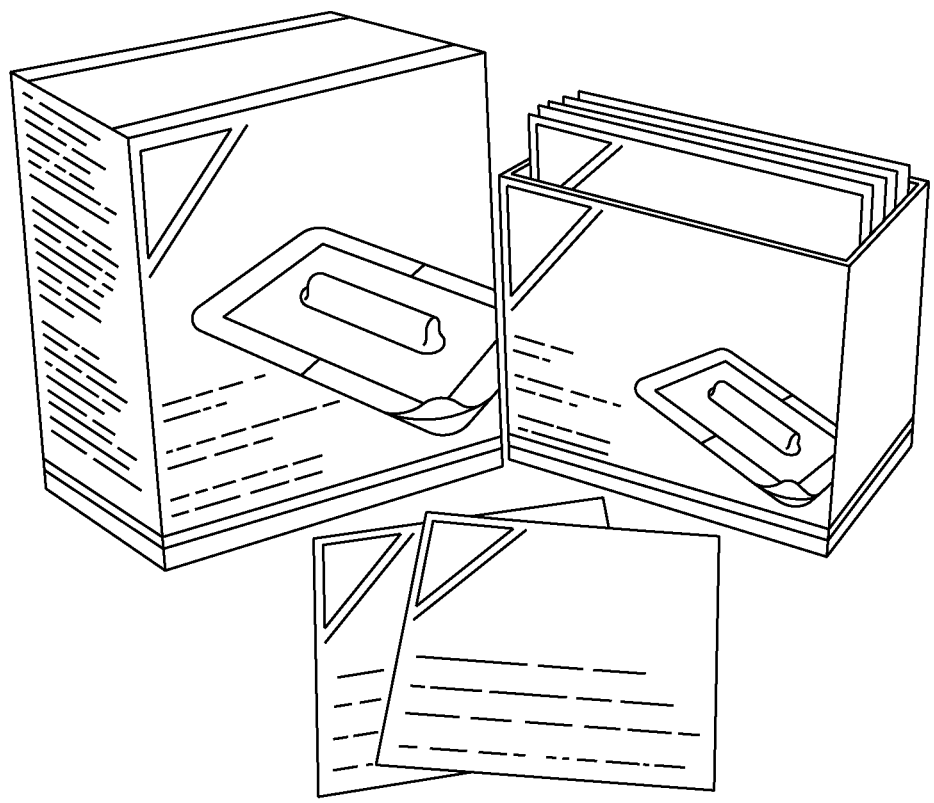
FIGS. 9-16 are schematic views showing exemplary use of the new and improved NPWT bandage shown in FIGS. 1-4 (note that in FIGS. 11 and 14-16, removable cap 100 (see below) is removed from the figures for clarity of illustration)
Figure 10:
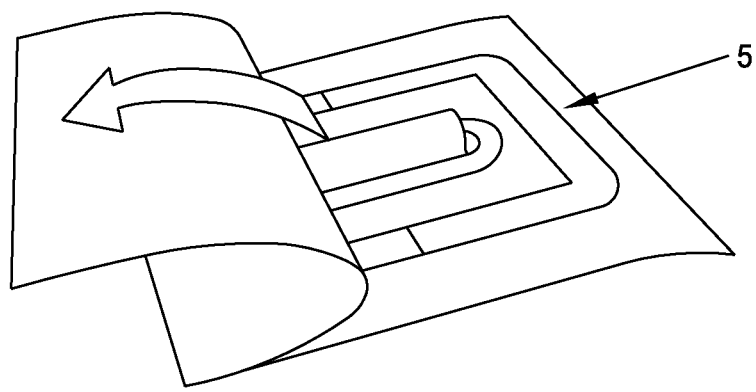

Note also that the prior art approaches of forming the pump body with dome-like or square pump configurations does not provide the pump body with an abrupt change of state—rather, these prior art dome-like or square pump configurations provide the pump body with a more gradual change of state between an expanded configuration and a collapsed configuration when the pressure differential between the pressure of the fluid within an inner chamber and atmospheric pressure changes. See FIG. 8, which is a graph showing the relationship between the diameter of the side wall of a pump body having a dome-like or square configuration and the pressure differential between the pressure of a fluid within an inner chamber of the pump body and atmospheric pressure.

As a result of deliberately configuring side wall 65 of pump body 60 of pump assembly 15 to exhibit this abrupt change of state, pump assembly 15 is able to provide improved pump efficiency, an automatic pressure indicator for indicating the level of negative pressure created, and an automatic pressure limiter for limiting the level of negative pressure created.

More particularly, by configuring pump body 60 of pump assembly 15 so that it will abruptly change state between its substantially fully expanded configuration and its substantially fully collapsed configuration when the pressure differential between the pressure of a fluid within inner chamber 70 and atmospheric pressure crosses a given threshold, pump assembly 15 effectively returns to its substantially fully expanded configuration as long as the pressure differential between the pressure of the fluid within inner chamber 70 and atmospheric pressure is below the given threshold. As a result, so long as the pressure differential between the fluid within inner chamber 70 and atmospheric pressure is below the given threshold, pump assembly 15 returns to its substantially fully expanded configuration between compressions (i.e., squeezes), and hence remains fully efficient as it applies a negative pressure to the wound chamber. This is in contrast to the performance of prior art devices where the pump body exhibits a gradual change of state between an expanded configuration and a collapsed configuration when the pressure differential between the pressure of a fluid within the inner chamber of the pump assembly changes, which makes the pump assembly progressively less efficient as it reduces the pressure within the wound chamber. This is because the pump body will progressively return less and less to its fully expanded configuration as negative pressure is created in the wound chamber, so that the pump assembly is able to evacuate less and less fluid with each squeeze of the pump body. In other words, with prior art devices, the pump assembly becomes less and less efficient as negative pressure is created in the wound chamber.

In a related manner, by configuring pump body 60 so that it will abruptly change state between its substantially fully expanded configuration and its substantially fully collapsed configuration when the pressure differential between the pressure of the fluid within inner chamber 70 and atmospheric pressure crosses a given threshold, pump assembly 15 is able to function as an automatic pressure indicator for indicating the level of negative pressure created, i.e., so long as pump body 60 of pump assembly 15 returns to its substantially fully expanded configuration between squeezes, it will be readily apparent to an observer that the pressure within inner chamber 70 (and hence the pressure within the wound chamber) will be less than a given level. This is in marked contrast to the performance of prior art devices where pump body 60 provides a gradual change of state between an expanded configuration and a collapsed configuration when the pressure differential between the pressure of a fluid within an inner chamber of the pump assembly changes, in which case the pump assembly is not able to function as an automatic pressure indicator for indicating the level of negative pressure created.

And also in a related manner, by configuring pump body 60 so that it will abruptly change state between its substantially fully expanded configuration and its substantially fully collapsed configuration when the pressure differential between the pressure of a fluid within inner chamber 70 and atmospheric pressure crosses a given threshold, pump assembly 15 is able to function as an automatic pressure limiter for limiting the level of negative pressure created since, as soon as pump body 60 assumes its substantially fully collapsed configuration, pump assembly 15 is no longer able to pump fluid from the wound chamber, essentially deactivating the pump assembly. This is in marked contrast to the performance of prior art devices where the pump body provides a gradual change of state between an expanded configuration and a collapsed configuration when the pressure differential between the pressure of a fluid within an inner chamber changes, since the pump assembly is not effectively deactivated at a given pressure differential.

It should be appreciated that the pressure differential required to transition pump body 60 between its substantially fully-expanded configuration and its substantially fully-collapsed configuration (i.e., the aforementioned "given threshold") may be "tuned" (i.e., tailored) to a particular level by varying one or more characteristics of pump body 60, e.g., by forming side wall 65 of pump body 60 out of a material having a particular durometer, by adjusting the thickness of side wall 65 of pump body 60, by adjusting the diameter of inner chamber 70 of pump body 60, etc.

In general, it has been found that excellent therapeutic results may be achieved when the pressure differential required to transition pump body 60 between its substantially fully-expanded configuration and its substantially fully-collapsed configuration (i.e., the aforementioned "given threshold") is between about 60 mm Hg and about 180 mm Hg. In other words, it has been found that excellent therapeutic results may be achieved where pump body 60 transitions between its substantially fully-expanded configuration (FIG. 5) and its substantially fully-collapsed configuration (FIG. 6) at a negative pressure of between about 60 mm Hg and about 180 mm Hg. It is believed that where pump body 60 transitions between its two states at a lower pressure (i.e., where pump body 60 transitions at a negative pressure lower than about 60 mm Hg), not enough suction is provided at the wound site to effectively draw contaminants and microbes away from the wound site and/or to effectively draw exudates away from the wound site and/or to promote beneficial biological responses at the wound site. It is also believed that where pump body 60 transitions between its two states at a higher pressure (i.e., where pump body 60 transitions at a negative pressure higher than about 180 mm Hg), the suction provided at the wound site may cause trauma to the tissue (e.g., blistering, capillary leakage, etc.).

In one preferred form of the invention, pump body 60 of pump assembly 15 is configured so that it abruptly transitions between its substantially fully expanded configuration and its substantially fully collapsed configuration when the pressure differential between the pressure of the fluid within inner chamber 70 and atmospheric pressure exceeds 80 mm Hg. Thus, in this form of the invention, as long as the negative pressure within the wound chamber is less than 680 mm Hg (assuming atmospheric pressure is 760 mm Hg), pump assembly 15 returns to its substantially fully expanded configuration between squeezes of the pump body and maintains its pump efficiency as it applies suction to the wound chamber, and as soon as the negative pressure within the wound chamber exceeds 680 mm Hg (assuming atmospheric pressure is 760 mm Hg), pump assembly 15 will assume its substantially fully collapsed configuration, acting as an automatic pressure indicator to indicate that the level of negative pressure created at the wound site has exceeded 80 mm Hg and automatically deactivating pump assembly 15 so that the level of negative pressure created at the wound site cannot exceed 80 mm Hg.

Note that inasmuch as pump body 60 of pump assembly 15 has a substantially cylindrical configuration, NPWT bandage 5 has a low profile.

Note also that inasmuch as pump body 60 of pump assembly 15 is configured to be squeezed between the thumb and forefinger of a user, the compressive force being applied to pump body 60 is applied parallel to the surface of the skin, so that no trauma is applied to the wound during use (i.e., during pumping of pump assembly 15). This is in marked contrast to prior art NPWT bandages which employ a dome-like configuration and require the compressive force to be applied toward the wound.

Exemplary Use

In one preferred form of the invention, and looking now at FIGS. 9-16, NPWT bandage 5 is intended to be used as follows.

First, an NPWT bandage 5 is removed from its box. In one form of the invention, each individual NPWT bandage 5 is contained in a separate sterile package, with multiple sterile packages contained in a box. See FIG. 9.

Figure 11:
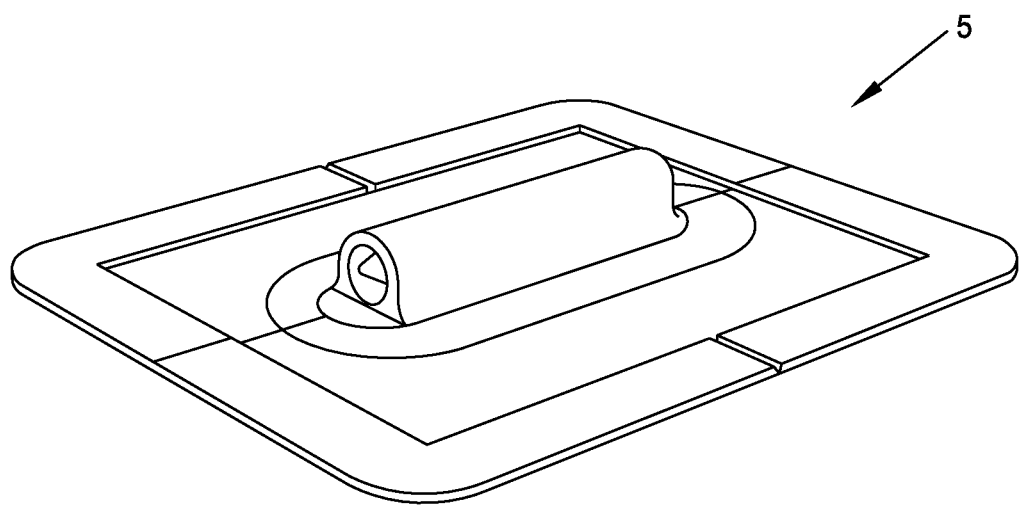
Figure 12:
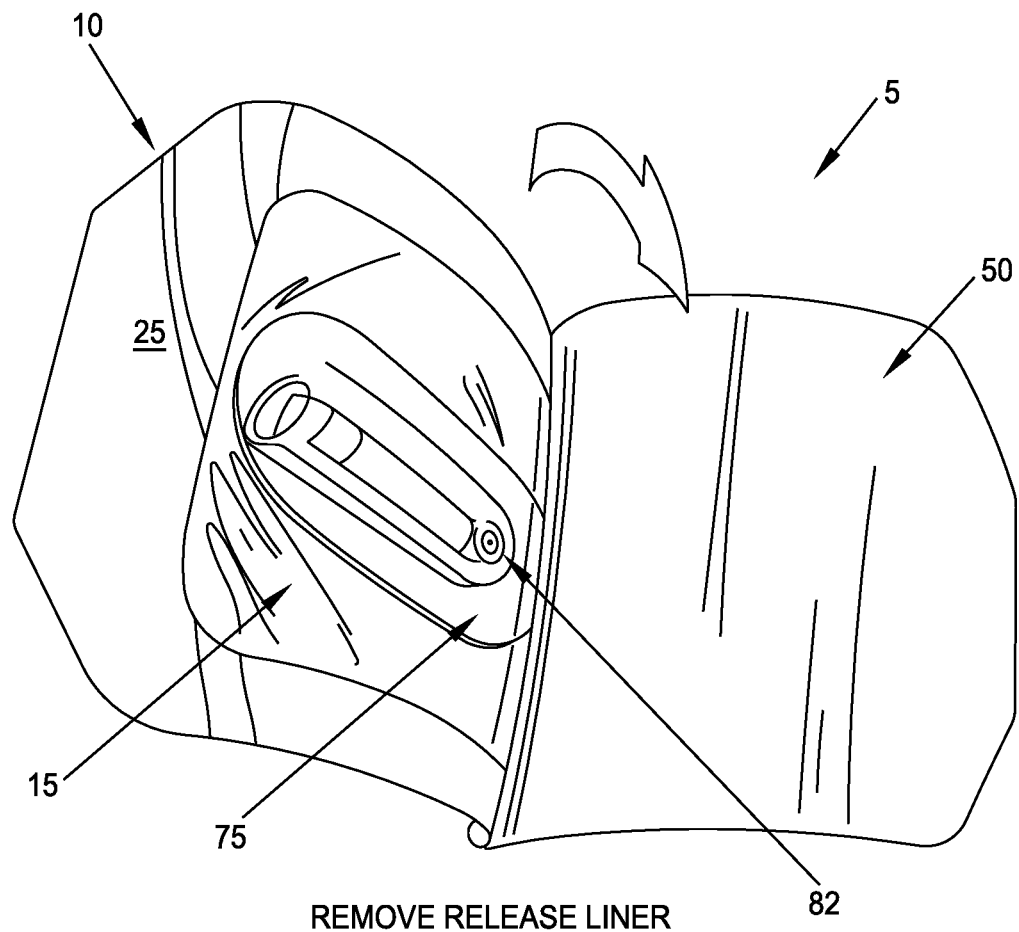
Figure 13:
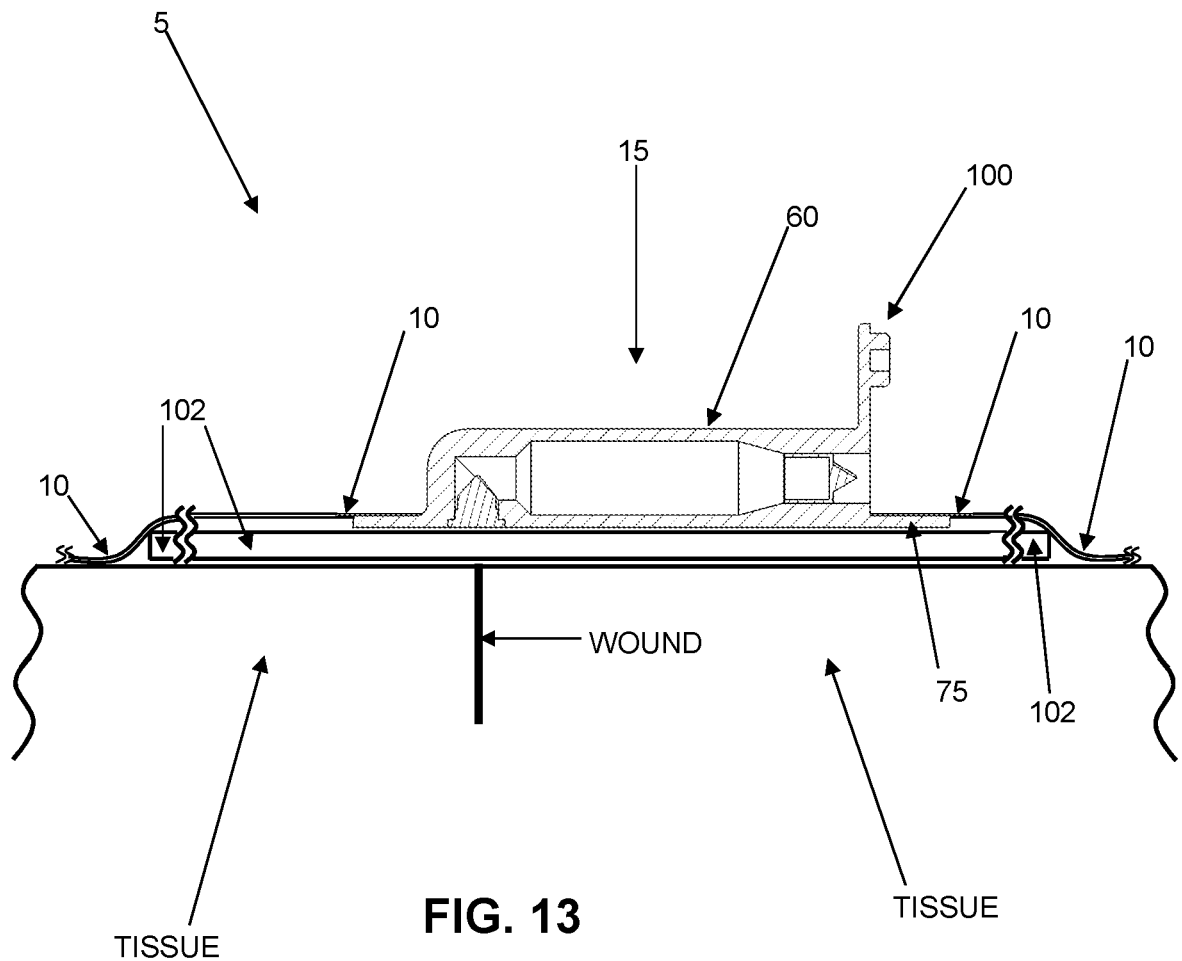
Figure 14:
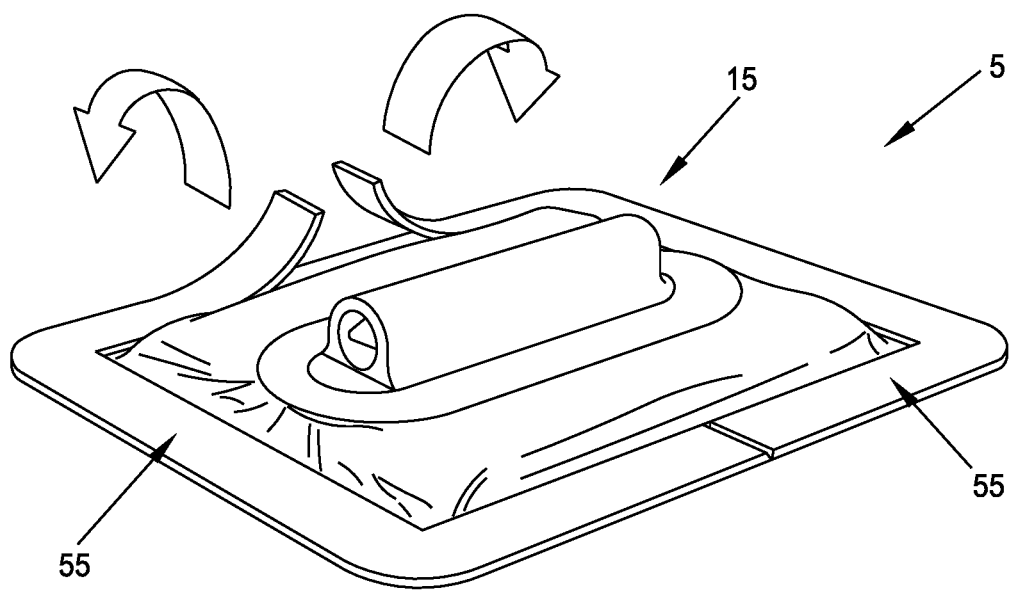
Figure 15:
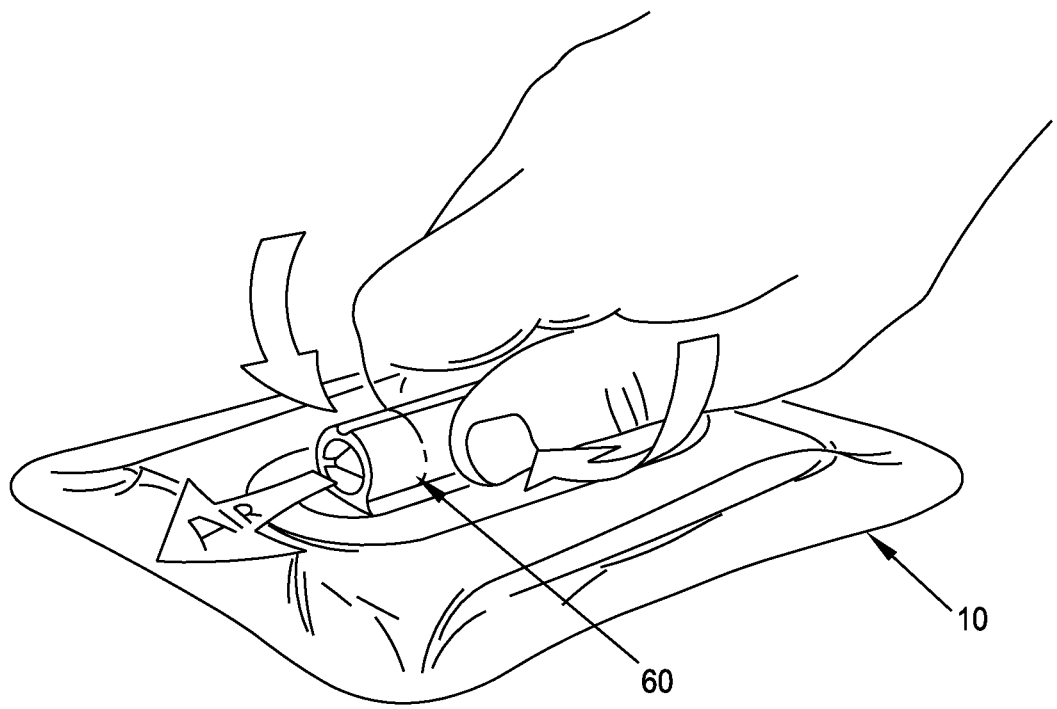
Figure 16:
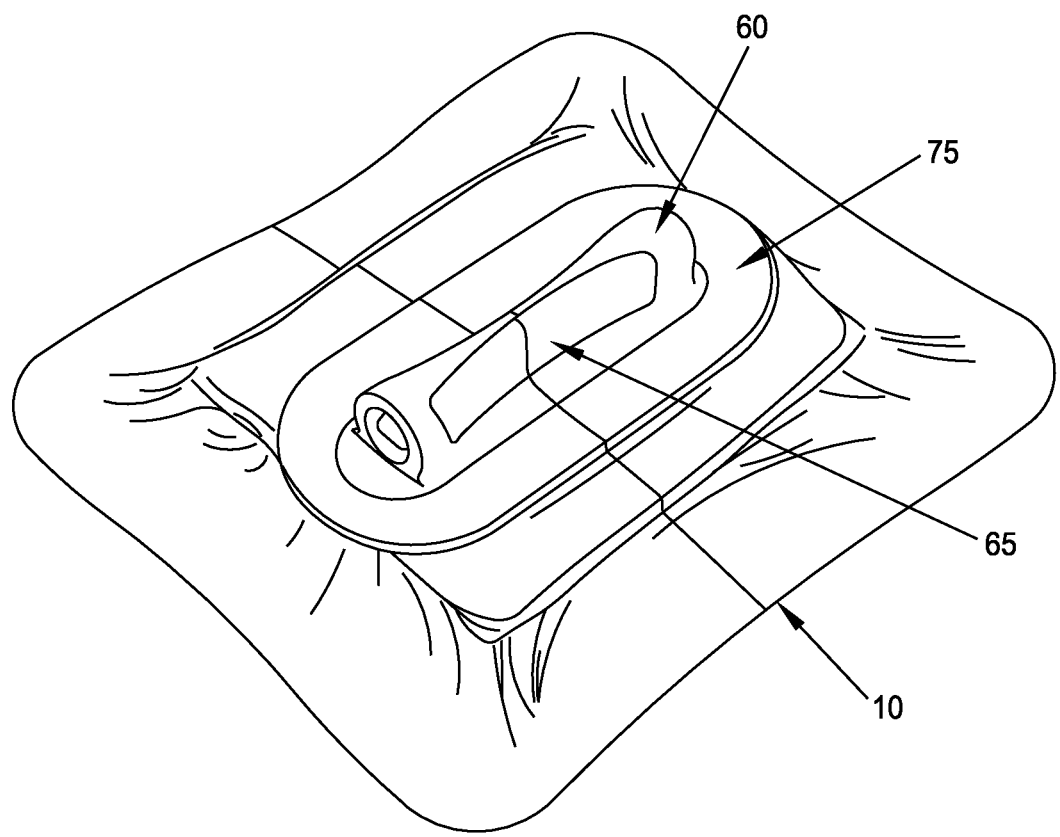
Figure 17:
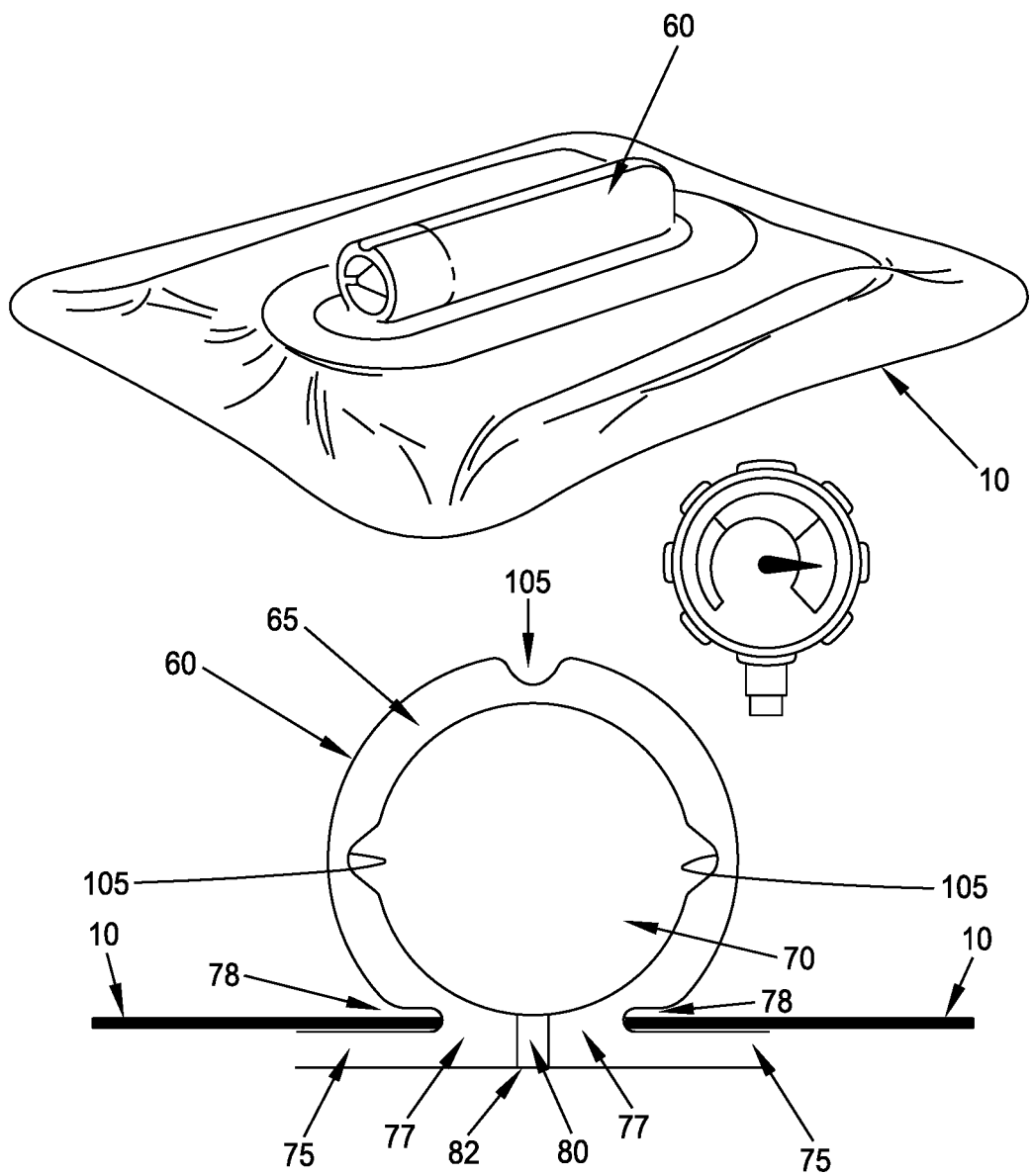
FIGS. 17-20 are schematic views showing another new and improved NPWT bandage formed in accordance with the present invention.
Figure 18:
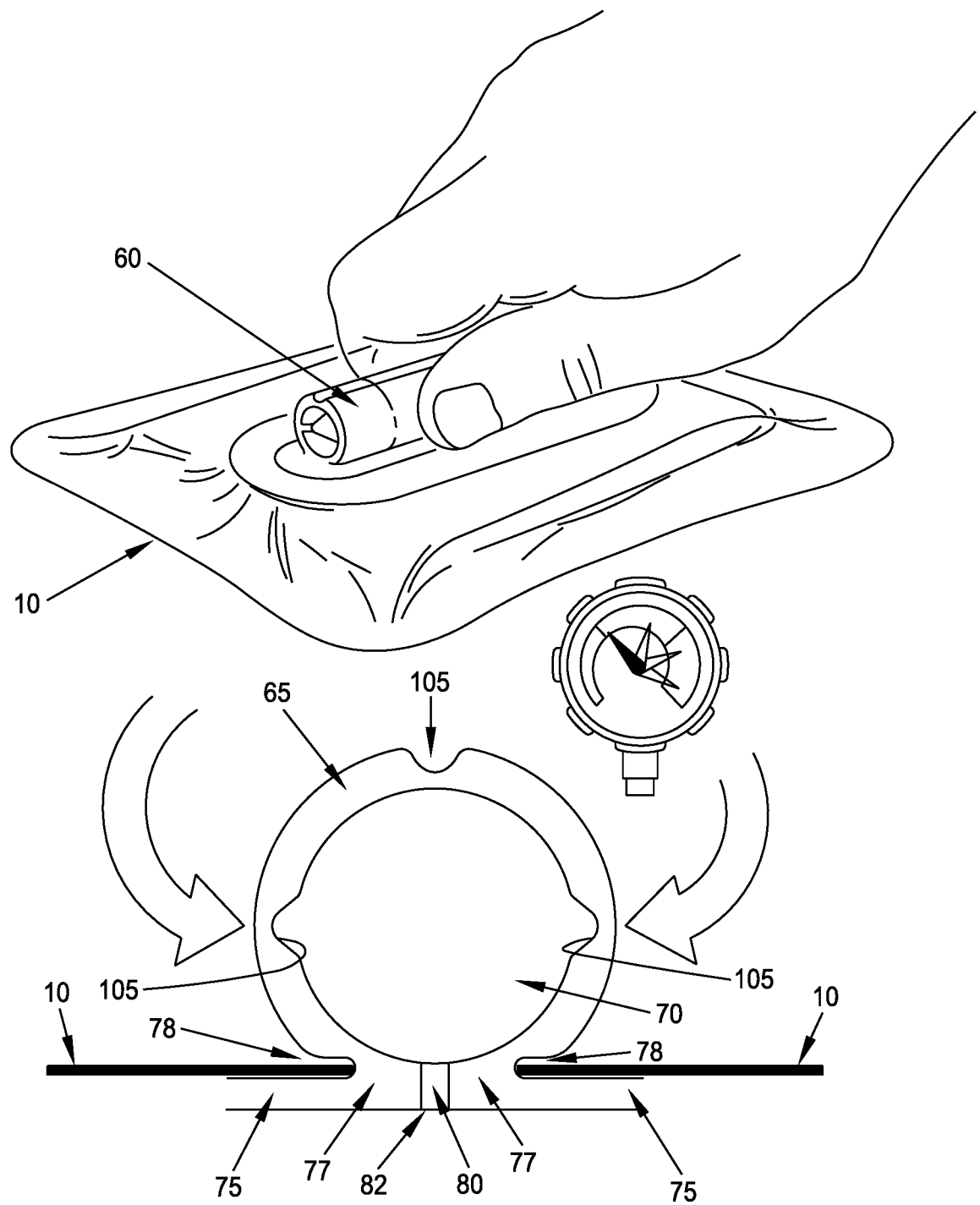
Figure 19:
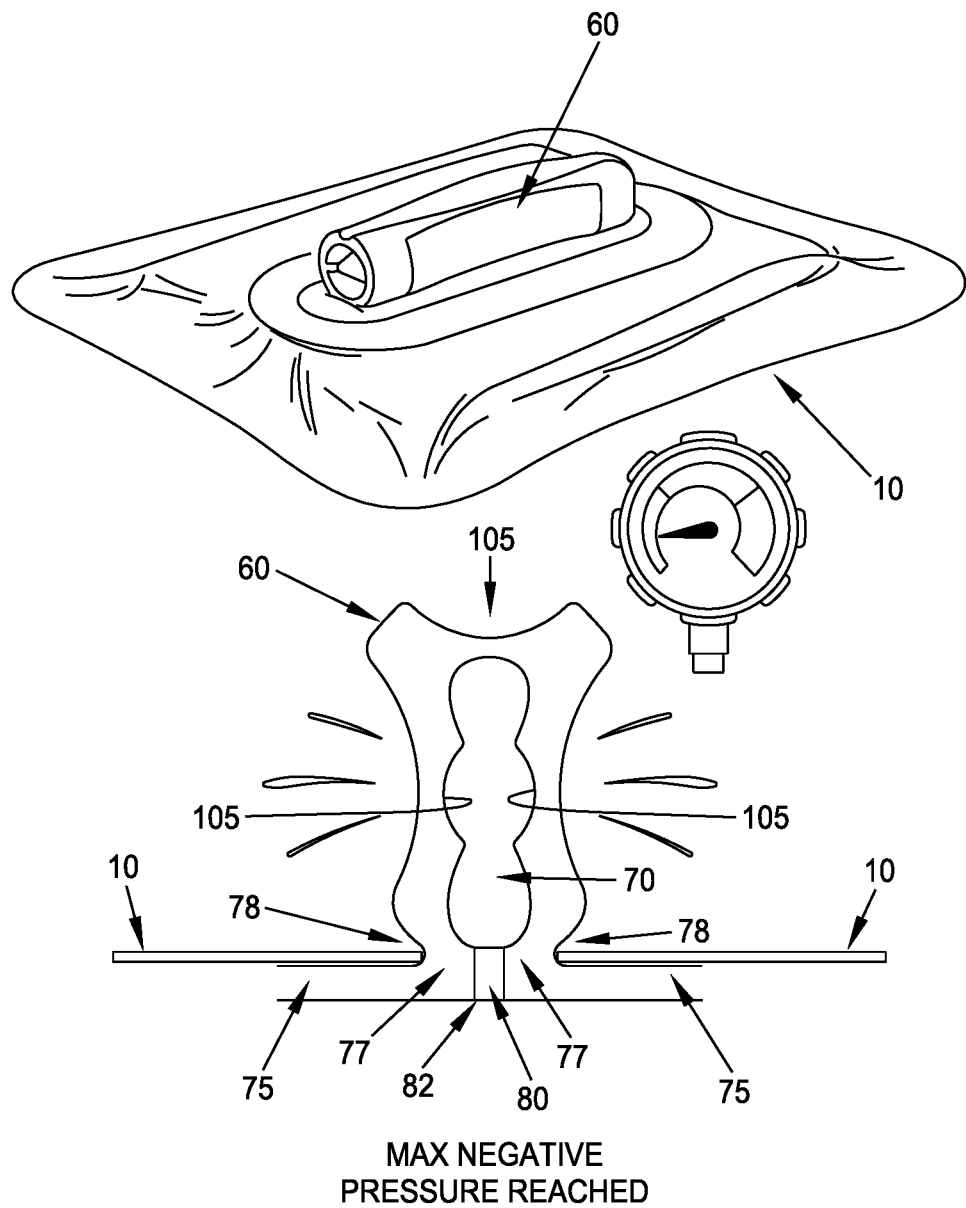
Figure 20:
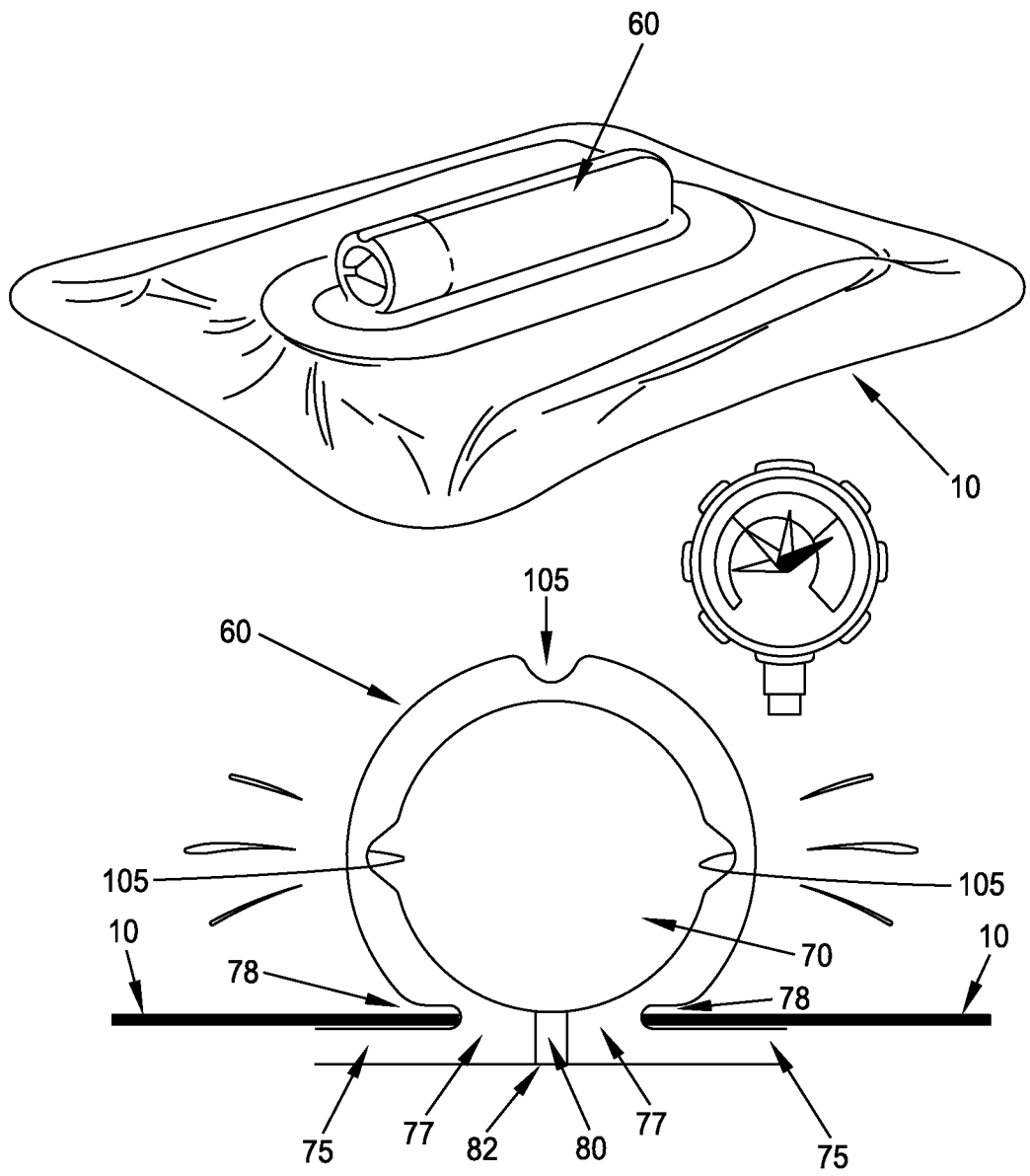
Figure 21:
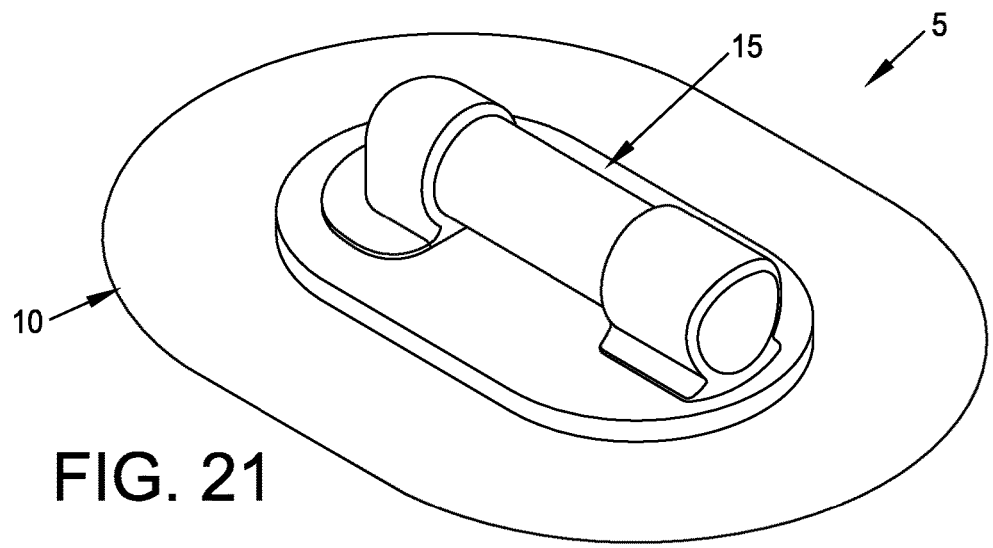
FIGS. 21-25 are schematic views showing another new and improved NPWT bandage formed in accordance with the present invention.
Figure 22:
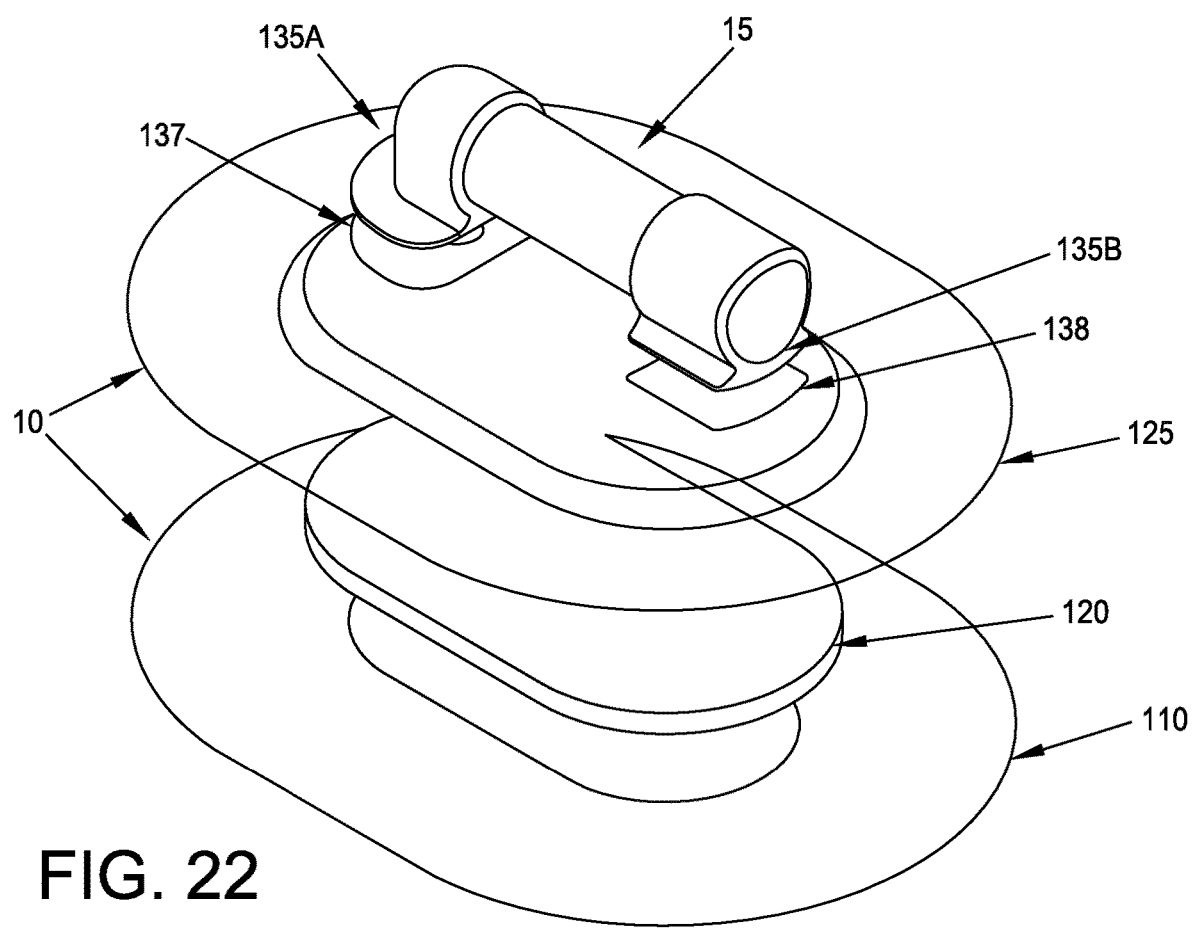
Figure 23:
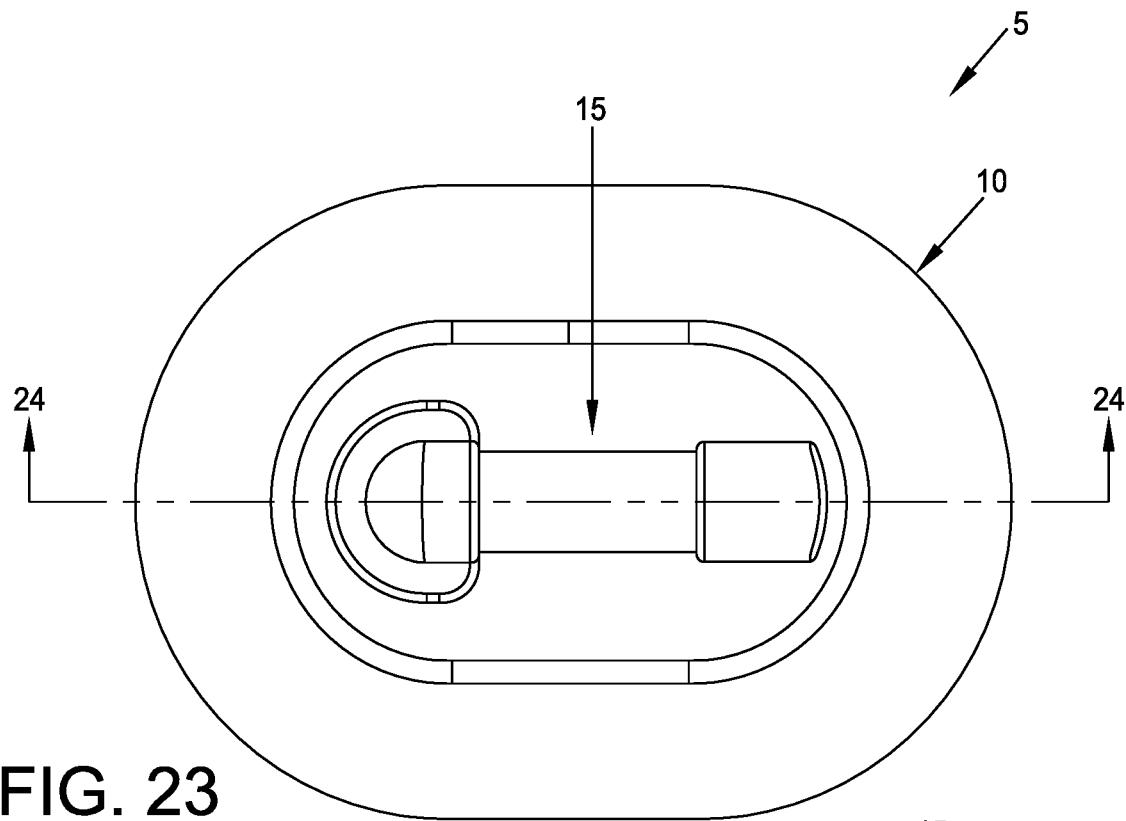
Figure 24:
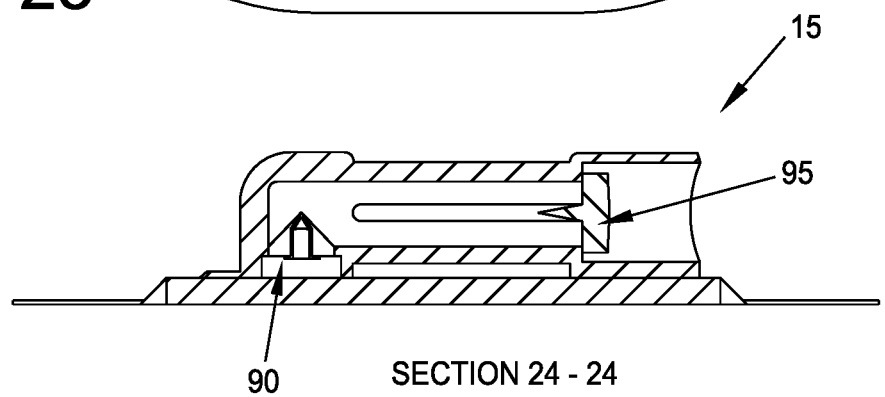
Figure 25:
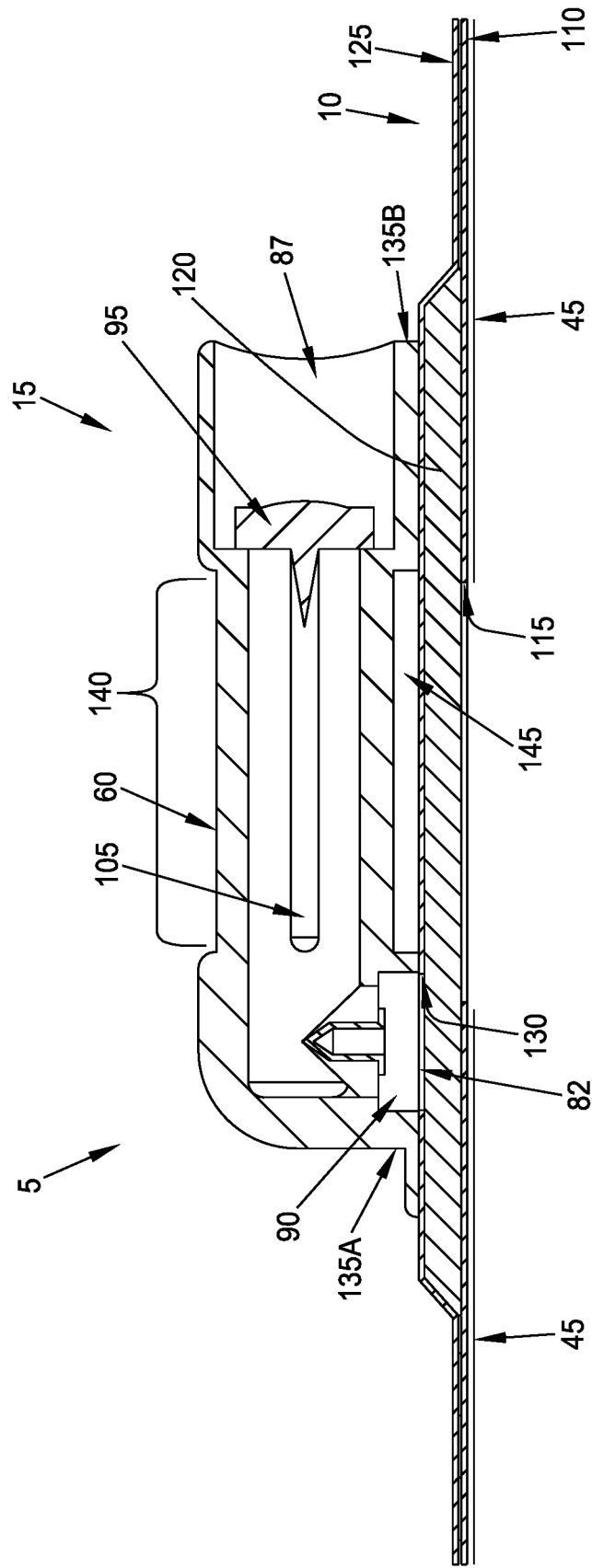

Next, an NPWT bandage 5 is removed from its sterile package (FIG. 10) so as to be ready for use (FIG. 11).

In order to apply NPWT bandage 5 to the wound site, release liner 50 is removed from wound-side surface 25 of membrane 10. See FIG. 12. Then NPWT bandage 5 is positioned against the skin of a patient so that wound-side surface 25 of membrane 10 is positioned against the wound, with adhesive 45 securing NPWT bandage 5 to the skin of the patient, thereby forming a substantially air-tight seal with the skin of the patient about the perimeter of the wound chamber. See FIG. 13.

Note that when NPWT bandage 5 is applied to the skin of the patient, wound-side port 82 of wound-side passageway 80 of pump assembly 15 is open to the wound chamber.

Note also that a layer of gauze (or other absorbent wound dressing) 102 may be placed on the wound site prior to placing NPWT bandage 5 on the skin of the patient, so that the layer of gauze (or other absorbent wound dressing) is interposed between the wound and wound-side passageway 80 of pump assembly 15. As a result, exudate emerging from the wound will be taken up by the gauze (or other absorbent wound dressing). Note that, if desired, the layer of gauze (or other absorbent wound dressing) 102 may be mounted to (i.e., secured to) the wound-side surface of membrane 10, e.g., such as at the time of manufacture, so that the layer of gauze (or other absorbent wound dressing) 102 is carried to the wound site by NPWT bandage 5 and is applied to the wound at the same time as the NPWT bandage 5.

Next, with NPWT bandage 5 secured to the skin of the patient, removable stiffener 55 is removed from atmosphere-side surface 30 of membrane 10. See FIG. 14.

At this point, NPWT bandage 5 may be used to apply negative pressure to the wound chamber. This is done by squeezing side wall 65 of pump body 60 between the thumb and forefinger of a user so as to compress pump body 60 into its substantially fully collapsed configuration, whereby to expel fluid (e.g., air, liquid, etc.) from inner chamber 70 of pump body 60 via atmosphere-side passageway 85 and atmosphere-side one-way valve 95. See FIG. 15. Note that fluid in inner chamber 70 of pump body 60 is prevented from exiting inner chamber 70 through wound-side passageway 80 due to the presence of wound-side one-way valve 90. Then side wall 65 of pump body 60 is released, allowing the resilient pump body 60 to return to its substantially fully expanded configuration, thereby creating a negative pressure within inner chamber 70 and wound-side passageway 80, such that fluid below wound-side surface 25 of membrane 10 (e.g., fluid within the wound chamber) is drawn into inner chamber 70 through wound-side passageway 85 and wound-side one-way valve 90. Note that air in the atmosphere is prevented from entering inner chamber 70 through atmosphere-side passageway 85 due to the presence of atmosphere-side one-way valve 95.

This process of squeezing and releasing side wall 65 of pump body 60 is repeated until pump body 60 of pump assembly 15 remains in its substantially fully collapsed configuration (i.e., side wall 65 of pump body 60 bows inwardly) even when side wall 65 of pump body 60 is not being manually compressed. See FIG. 16. When pump body 60 of pump assembly 15 remains in its substantially fully collapsed configuration even when side wall 65 of pump body 60 is not being manually compressed, an observer will know that the pressure differential between the pressure of the fluid within inner chamber 70 (and the wound chamber) and atmospheric pressure exceeds the desired threshold, indicating that the desired level of negative pressure has been achieved at the wound site. Note that when pump body 60 of pump assembly 15 remains in its substantially fully collapsed configuration even when side wall 65 of pump body 60 is not being manually compressed, pump assembly 15 will have been effectively deactivated, since it will be impossible to continue using the pump assembly with side wall 65 in its substantially fully collapsed configuration.

At this point removable cap 100 may be used to seal atmosphere-side port 87 of atmosphere-side passageway 85.

NPWT bandage 5 is left in place on the wound for an appropriate period of time (e.g., a few days) so as to shield the wound from contaminants and microbes during healing, draw exudates out of the wound, and promote beneficial biological responses at the wound site. In the event that leakage should cause the negative pressure created in the wound chamber to fall below the given threshold (which will be apparent to an observer by virtue of the fact that side wall 65 of pump body 60 will return to its substantially fully-expanded configuration), atmosphere-side port 87 of atmosphere-passageway 85 may be unsealed (i.e., by removing removable cap 100) and then pump assembly 15 may be used in the manner discussed above to re-establish the desired negative pressure in the wound chamber (i.e., by repeatedly squeezing and releasing side wall 65 of pump body 60).

When appropriate, NPWT bandage 5 may be removed from the skin of the patient by simply peeling membrane 10 away from the skin of the patient.

Pump Body with Notches to Enhance the Substantially "Binary State" Behavior of the Pump Body As noted above, pump body 60 of pump assembly 15 is preferably specifically configured so that the pump body will abruptly change state between (i) a substantially fully expanded configuration where side wall 65 of pump body 60 and inner chamber 70 of pump body 60 have a substantially circular cross-section (see FIG. 5) when the pressure differential between the pressure of the fluid within inner chamber 70 and atmospheric pressure is below a given threshold, and (ii) a substantially fully collapsed configuration where side wall 65 of pump body 60 bows inwardly (see FIG. 6) when the pressure differential between the pressure of the fluid within inner chamber 70 and atmospheric pressure exceeds a given threshold.

As also noted above, this substantially "binary state" behavior of pump body 60 is achieved by forming the pump body with a substantially circular cross-section, which gives the body an "over-the-center" deformation characteristic, i.e., so that the side wall of pump body 60 has a "failure" mode where it abruptly transitions from a substantially fully expanded configuration to a substantially fully collapsed configuration, and has a "restoration" mode where it abruptly transitions from a substantially fully collapsed configuration to a substantially fully expanded configuration. See FIG. 7. As noted above, by forming pump assembly 15 so that side wall 65 of pump body 60 and pump flange 75 merge at a neck 77 (FIG. 5), with neck 77 having a relatively small width relative to the full diameter of pump body 60, and with recesses 78 extending inwardly between membrane 10 and pump body 60, pump body 60 has a substantially circular cross-section over substantially its entire circumference, with pump body 60 free to radially compress/radially expand with minimal interference from pump flange 75, so that pump body 60 can exhibit substantially "binary state" behavior.

If desired, pump body 60 can be modified so as to enhance the substantially "binary state" behavior of the pump body.

By way of example but not limitation, and looking now at FIGS. 17-20, notches 105 can be formed in pump body 60 (e.g., at the "9 o'clock", "12 o'clock" and "3 o'clock" positions) so as to enhance the substantially "binary state" behavior of the pump body by further inducing pump body 60 to assume only its substantially fully expanded configuration or its substantially fully collapsed configuration. Note that the more that pump body 60 exhibits true "binary state" behavior, the more that pump efficiency will improve and the better that pump assembly 15 will serve as an automatic pressure indicator and as an automatic pressure limiter.

NPWT Bandage Incorporating Gauze (or Other Absorbent Wound Dressing) and Utilizing an Improved Pump Assembly Looking next at FIGS. 21-25, there is shown another negative pressure wound therapy (NPWT) bandage 5 formed in accordance with the present invention. The NPWT bandage 5 shown in FIGS. 21-25 is substantially the same as the NPWT bandage 5 shown in FIGS. 1-16, and the NPWT bandage 5 shown in FIGS. 17-20, except that (i) in the construction shown in FIGS. 21-25, membrane 10 comprises multiple layers which incorporate gauze (or other absorbent wound dressing), and (ii) in the construction shown in FIGS. 21-25, pump assembly 15 has a modified construction and is secured to membrane 10 using a different approach.

More particularly, in this form of the invention, membrane 10 comprises a lower skin-contacting polyurethane layer 110 having a center opening 115, an intermediate foam (or gauze or other absorbent wound dressing) layer 120 for disposition over center opening 115 of lower skin-contacting polyurethane layer 110, and an upper polyurethane layer 125 for disposition over intermediate foam layer 120 and lower skin-contacting polyurethane layer 110. In the preferred form of the invention, upper polyurethane layer 125 is formed out of a substantially air-impermeable material. And, in the preferred form of the invention, upper polyurethane layer 125 and lower skin-contacting polyurethane layer 110 have the same size outer perimeter, so that upper polyurethane layer 125 does not contact the skin of the patient. The outer perimeters of upper polyurethane layer 125 and lower skin-contacting polyurethane layer 110 are secured to one another, capturing intermediate foam layer 120 therebetween. Intermediate foam layer 120 has an outer perimeter which is (i) larger than the perimeter of center opening 115 of lower skin-contacting polyurethane layer 110, and (ii) smaller than the outer perimeter of the outer perimeters of lower skin-contacting polyurethane layer 110 and upper polyurethane layer 125. In this way, when NPWT bandage 5 has its center opening 115 of lower skin-contacting polyurethane layer 110 positioned over a wound, fluid from the wound can pass through center opening 115 of lower skin-contacting polyurethane layer 110 to reach intermediate foam layer 120. It will be appreciated that adhesive 45 is positioned on the wound side surface of lower skin-contacting polyurethane layer 110 so that a substantially air-tight seal may be established by NPWT bandage 5 about the perimeter of a wound (i.e., so as to form the aforementioned wound chamber). An opening 130 is formed in upper polyurethane layer 125, and overlaps center opening 115 of lower skin-contacting polyurethane layer 110, so that wound-side passageway 80 of pump assembly 15 can access fluid (e.g., air, liquid, etc.) within the wound chamber (i.e., via opening 130 in upper polyurethane layer 125, the openings in intermediate foam layer 120, and center opening 115 of lower skin-contacting polyurethane layer 110) for evacuation during pumping of pump assembly 15.

The pump assembly 15 utilized in the NPWT bandage 5 of FIGS. 21-25 is generally similar to the pump assembly 15 described above, except that it comprises a pair of pedestals 135A, 135B for mounting pump assembly 15 to membrane 10. More particularly, pedestal 135A comprises one end of pump body 60 and is adhered (e.g., by an adhesive 137) to the upper surface of membrane 10 (i.e., to the upper surface of upper polyurethane layer 125) so that wound-side passageway 80 and wound-side one-way valve 90 are aligned with opening 130 in upper polyurethane layer 125 (and hence in fluid communication with the wound chamber). Pedestal 135B comprises the other end of pump body 60 and is adhered (e.g., by an adhesive 138) to the upper surface of membrane 10 (i.e., to the upper surface of upper polyurethane layer 125). The intervening portion 140 of pump body 60 sits suspended between pedestal 135A and pedestal 135B, elevated above upper polyurethane layer 125 of membrane 10, so that a space 145 is formed between intervening portion 140 of pump body 60 and upper polyurethane layer 135 of membrane 10. Inasmuch as intervening portion 140 of pump body 60 is not mounted directly to membrane 10, but is instead suspended above membrane 10 by means of pedestals 135A and 135B, intervening portion 140 of pump body 60 can be formed with a true circular cross-section, whereby to enhance the substantially "binary state" behavior of the NPWT bandage. It will be appreciated that pump body 60 may incorporate one or more of the aforementioned notches 105 so as to further enhance the substantially "binary state" behavior of the NPWT bandage.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A negative pressure wound therapy (NPWT) bandage for applying negative pressure to a wound, said NPWT bandage comprising:
   a membrane configured for disposition over a wound so as to form a wound chamber between said membrane and the wound, said membrane comprising a wound-side surface, an atmosphere-side surface, and an opening extending through said membrane from said wound-side surface to said atmosphere-side surface; and
   a pump assembly carried by said membrane, said pump assembly comprising:
      a pump body comprising a wall structure which forms a hollow pump chamber, wherein at least a portion of said wall structure is resilient, wherein two notches are formed on an internal surface of said wall structure of said pump body;
      a wound-side passageway extending through said wall structure and communicating with the wound chamber through said opening formed in said membrane;
      a wound-side one-way valve disposed in said wound-side passageway, said wound-side one-way valve being configured to allow fluid to flow through said wound-side passageway from the wound chamber to said pump chamber but to prevent fluid from flowing through said wound-side passageway from said pump chamber to the wound chamber;
      an atmosphere-side passageway extending through said wall structure and connecting said pump chamber and the atmosphere; and
      an atmosphere-side one-way valve disposed in said atmosphere-side passageway, said atmosphere-side one-way valve being configured to allow fluid to flow through said atmosphere-side passageway from said pump chamber to the atmosphere but to prevent fluid from flowing through said atmosphere-side passageway from the atmosphere to said pump chamber;
   such that when a compressive force is applied to said wall structure of said pump body, fluid within said pump chamber will be forced out of said pump chamber via said atmosphere-side passageway, and when the compressive force applied to said wall structure of said pump body is thereafter reduced, the resiliency of the wall structure will cause the pump body to assume a substantially fully expanded configuration, whereby fluid within the wound chamber will be drawn into said pump chamber through said wound-side passageway.

2. An NPWT bandage according to claim 1 wherein said membrane comprises a plurality of layers.

3. An NPWT bandage according to claim 2 wherein said membrane comprises a substantially air-impermeable layer and an absorbent layer, wherein said absorbent layer is disposed on the wound side of said substantially air-impermeable layer.

4. An NPWT bandage according to claim 3 further comprising an additional layer, wherein said absorbent layer is disposed between said substantially air-impermeable layer and said additional layer.

5. An NPWT bandage according to claim 1 wherein a portion of said pump assembly extends through said opening formed in said membrane.

6. An NPWT bandage according to claim 5 wherein said pump assembly comprises a flange connected to said pump body, and further wherein said flange is secured to said wound-side surface of said membrane and said pump body extends through said opening formed in said membrane.

7. An NPWT bandage according to claim 6 wherein said flange is formed integral with said pump body.

8. An NPWT bandage according to claim 7 wherein a neck is formed between said pump body and said flange, and further wherein a pair of recesses extend inwardly between said pump body and said flange.

9. An NPWT bandage according to claim 1 wherein said pump assembly is mounted to said membrane by a pair of pedestals, and further wherein one of said pedestals comprises said wound-side passageway.

10. An NPWT bandage according to claim 9 wherein said pump body is suspended between said pair of pedestals and spaced from said membrane.

11. An NPWT bandage according to claim 1 wherein said pump assembly comprises a removable cap for selectively closing off said atmosphere-side passageway.

12. An NPWT bandage according to claim 1 wherein said wound-side surface of said membrane comprises an adhesive.

13. An NPWT bandage according to claim 12 wherein a release liner is disposed on said wound-side surface of said membrane atop said adhesive.

14. An NPWT bandage according to claim 1 wherein a removable stiffener is disposed on said atmosphere-side surface of said membrane.

15. An NPWT bandage according to claim 1 wherein, when the pressure differential between the pressure within said pump chamber and atmospheric pressure is below a predetermined threshold, said pump body of said pump assembly will assume a substantially fully expanded configuration, and when said pressure differential between the pressure within said pump chamber and atmospheric pressure is above said predetermined threshold, said pump body of said pump assembly will assume a substantially fully collapsed configuration.

16. An NPWT bandage according to claim 15 wherein said pump body abruptly changes state between said substantially fully expanded configuration and said substantially fully collapsed configuration, and between said substantially fully collapsed configuration and said substantially fully expanded configuration, as said pressure differential crosses said predetermined threshold so as to effectively constitute a substantially "binary state" device.

17. An NPWT bandage according to claim 15 wherein said predetermined threshold is between about 60 mm Hg and about 180 mm Hg.

18. An NPWT bandage according to claim 15 wherein said pump body is configured so as to provide an "over-the-center" deformation characteristic.

19. An NPWT bandage according to claim 1 wherein said pump body comprises a substantially circular cross-section.

20. An NPWT bandage according to claim 1 wherein said pump body comprises a substantially oval cross-section.

21. An NPWT bandage according to claim 15 wherein (i) said wall structure of said pump body and said pump chamber comprise a substantially circular cross-section when said pressure differential between the pressure within said pump chamber and atmospheric pressure is below said predetermined threshold, and (ii) said wall structure of said pump body bows inwardly when said pressure differential between the pressure within said pump chamber and atmospheric pressure exceeds said predetermined threshold.

22. An NPWT bandage according to claim 15 wherein said pump assembly comprises a removable cap for selectively closing off said atmosphere-side passageway.

23. An NPWT bandage according to claim 15 wherein said wound-side surface of said membrane comprises an adhesive.

24. An NPWT bandage according to claim 23 wherein a release liner is disposed on said wound-side surface of said membrane atop said adhesive.

25. An NPWT bandage according to claim 15 wherein a removable stiffener is disposed on said atmosphere-side surface of said membrane.

26. An NPWT bandage according to claim 15 wherein said pump assembly comprises a flange connected to said pump body, and further wherein said flange is secured to said wound-side surface of said membrane and said pump body extends through said opening formed in said membrane.

27. An NPWT bandage according to claim 26 wherein said flange is formed integral with said pump body.

28. An NPWT bandage according to claim 15 wherein notches are formed in said wall structure of said pump body so as to facilitate substantially "binary state" behavior.

29. An NPWT bandage according to claim 1 wherein one notch is formed on an external surface of said wall structure of said pump body.

30. A negative pressure wound therapy (NPWT) bandage for applying negative pressure to a wound, said NPWT bandage comprising:
a membrane configured for disposition over a wound so as to form a wound chamber between said membrane and the wound, said membrane comprising a wound-side surface, an atmosphere-side surface, and an opening extending through said membrane from said wound-side surface to said atmosphere-side surface; and
a pump assembly carried by said membrane, said pump assembly comprising:
a pump body comprising a wall structure disposed about a pump chamber, wherein at least a portion of said wall structure is resilient;
a wound-side passageway extending through said wall structure and communicating with the wound chamber through said opening formed in said membrane;
a wound-side one-way valve disposed in said wound-side passageway, said wound-side one-way valve being configured to allow fluid to flow through said wound-side passageway from the wound chamber to said pump chamber but to prevent fluid from flowing through said wound-side passageway from said pump chamber to the wound chamber;
an atmosphere-side passageway extending through said wall structure and connecting said pump chamber and the atmosphere; and
an atmosphere-side one-way valve disposed in said atmosphere-side passageway, said atmosphere-side one-way valve being configured to allow fluid to flow through said atmosphere-side passageway from said pump chamber to the atmosphere but to prevent fluid from flowing through said atmosphere-side passageway from the atmosphere to said pump chamber;
wherein said pump assembly is mounted to said membrane by a pair of pedestals, and further wherein one of said pedestals comprises said wound-side passageway;
such that when a compressive force is applied to said wall structure of said pump body, fluid within said pump chamber will be forced out of said pump chamber via said atmosphere-side passageway, and when the compressive force applied to said wall structure of said pump body is thereafter reduced, the resiliency of the wall structure will cause the pump body to assume a substantially fully expanded configuration, whereby fluid within the wound chamber will be drawn into said pump chamber through said wound-side passageway.

31. An NPWT bandage according to claim 30 wherein said pump body is suspended between said pair of pedestals and spaced from said membrane.

32. An NPWT bandage according to claim 30 wherein said membrane comprises a plurality of layers.

33. An NPWT bandage according to claim 32 wherein said membrane comprises a substantially air-impermeable layer and an absorbent layer, wherein said absorbent layer is disposed on the wound side of said substantially air-impermeable layer.

34. An NPWT bandage according to claim 33 further comprising an additional layer, wherein said absorbent layer is disposed between said substantially air-impermeable layer and said additional layer.

35. An NPWT bandage according to claim 30 wherein said pump assembly comprises a removable cap for selectively closing off said atmosphere-side passageway.

36. An NPWT bandage according to claim 30 wherein said wound-side surface of said membrane comprises an adhesive.

37. An NPWT bandage according to claim 36 wherein a release liner is disposed on said wound-side surface of said membrane atop said adhesive.

38. An NPWT bandage according to claim 30 wherein a removable stiffener is disposed on said atmosphere-side surface of said membrane.

39. An NPWT bandage according to claim 30 wherein, when the pressure differential between the pressure within said pump chamber and atmospheric pressure is below a predetermined threshold, said pump body of said pump assembly will assume a substantially fully expanded configuration, and when said pressure differential between the pressure within said pump chamber and atmospheric pressure is above said predetermined threshold, said pump body of said pump assembly will assume a substantially fully collapsed configuration.

40. An NPWT bandage according to claim 39 wherein said pump body abruptly changes state between said substantially fully expanded configuration and said substantially fully collapsed configuration, and between said substantially fully collapsed configuration and said substantially fully expanded configuration, as said pressure differential crosses said predetermined threshold so as to effectively constitute a substantially "binary state" device.

41. An NPWT bandage according to claim 39 wherein said predetermined threshold is between about 60 mm Hg and about 180 mm Hg.

42. An NPWT bandage according to claim 39 wherein said pump body is configured so as to provide an "over-the-center" deformation characteristic.

43. An NPWT bandage according to claim 30 wherein said pump body comprises a substantially circular cross-section.

44. An NPWT bandage according to claim 30 wherein said pump body comprises a substantially oval cross-section.

45. An NPWT bandage according to claim 39 wherein (i) said wall structure of said pump body and said pump chamber comprise a substantially circular cross-section when said pressure differential between the pressure within said pump chamber and atmospheric pressure is below said predetermined threshold, and (ii) said wall structure of said pump body bows inwardly when said pressure differential between the pressure within said pump chamber and atmospheric pressure exceeds said predetermined threshold.

46. An NPWT bandage according to claim 39 wherein said pump assembly comprises a removable cap for selectively closing off said atmosphere-side passageway.

47. An NPWT bandage according to claim 39 wherein said wound-side surface of said membrane comprises an adhesive.

48. An NPWT bandage according to claim 47 wherein a release liner is disposed on said wound-side surface of said membrane atop said adhesive.

49. An NPWT bandage according to claim 39 wherein a removable stiffener is disposed on said atmosphere-side surface of said membrane.

50. An NPWT bandage according to claim 39 wherein notches are formed in said wall structure of said pump body so as to facilitate substantially "binary state" behavior.

51. An NPWT bandage according to claim 30 wherein notches are formed in said wall structure of said pump body.

52. An NPWT bandage according to claim 51 wherein two notches are formed on an internal surface of said wall structure of said pump body.

53. An NPWT bandage according to claim 51 wherein one notch is formed on an external surface of said wall structure of said pump body.

* * * * *